United States Patent
Deransart et al.

(10) Patent No.: US 12,343,262 B2
(45) Date of Patent: Jul. 1, 2025

(54) CONVERTIBLE STEM/FRACTURE STEM

(71) Applicant: TORNIER SAS, Montbonnot-Saint-Martin (FR)

(72) Inventors: Pierric Deransart, Saint Martin d'Uriage (FR); Cyrille Aroun Koumar Fleury, Lyons (FR); Vincent Gaborit, Saint Martin d'Hères (FR); Pascal Boileau, Nice (FR); Christopher R. Chuinard, Traverse City, MI (US); Philippe Clavert, Illkirch Graffenstaden (FR); Luc Favard, Montlouis (FR); James Kelly, San Francisco, CA (US); Sumant Krishnan, Dallas, TX (US); Francois Sirveaux, Villers les Nancy (FR)

(73) Assignee: TORNIER SAS, Montbonnot-Saint-Martin (FR)

( * ) Notice: Subject to any disclaimer, the term of this patent is extended or adjusted under 35 U.S.C. 154(b) by 902 days.

(21) Appl. No.: 17/450,710

(22) Filed: Oct. 13, 2021

(65) Prior Publication Data
US 2022/0023055 A1    Jan. 27, 2022

Related U.S. Application Data

(60) Continuation of application No. 16/554,013, filed on Aug. 28, 2019, now Pat. No. 11,173,037, which is a
(Continued)

(30) Foreign Application Priority Data

Dec. 10, 2014    (FR) ...................... 1462206

(51) Int. Cl.
*A61F 2/40* (2006.01)
*A61F 2/30* (2006.01)

(52) U.S. Cl.
CPC .. *A61F 2/4014* (2013.01); *A61F 2002/30607* (2013.01); *A61F 2002/4022* (2013.01);
(Continued)

(58) Field of Classification Search
CPC ........ A61F 2002/048; A61F 2002/9665; A61F 2210/009; A61M 27/008
See application file for complete search history.

(56) References Cited

U.S. PATENT DOCUMENTS

| | | |
|---|---|---|
| 3,314,420 A | 4/1967 | Smith et al. |
| D243,286 S | 2/1977 | Deyerle |

(Continued)

FOREIGN PATENT DOCUMENTS

| | | |
|---|---|---|
| CA | 211535 | 5/2022 |
| CA | 211538 | 5/2022 |

(Continued)

OTHER PUBLICATIONS

Med Gadget, "Tornier Announces First Implant in U.S. Trial of Its Simpliciti Stemless Shoulder Joint Replacement System", first available Aug. 5, 2011. (https://Avwww.medgadget.com/2011/08/tornier-announces-first-implant-in-u-s-trial-of-its-simpliciti-stemless-shoulder-joint-replacement-system.html) (Year: 2011), 1 page.

(Continued)

*Primary Examiner* — Bruce E Snow
(74) *Attorney, Agent, or Firm* — DUANE MORRIS LLP

(57) ABSTRACT

A humeral anchor for a shoulder prosthesis is disclosed. The humeral anchor includes a distal portion configured to be anchored in a proximal region of a humerus and a proximal portion, the proximal portion including a proximal face, where the proximal face includes an engagement feature configured to directly couple to a reverse shoulder insert having a concave proximal portion, and wherein the proximal face is further configured to directly couple with an
(Continued)

anatomical shoulder insert having a convex proximal portion.

22 Claims, 36 Drawing Sheets

Related U.S. Application Data division of application No. 15/532,035, filed as application No. PCT/US2015/065126 on Dec. 10, 2015, now Pat. No. 10,433,967.

(52) U.S. Cl.
CPC ............... *A61F 2002/4051* (2013.01); *A61F 2002/4085* (2013.01)

(56) References Cited

U.S. PATENT DOCUMENTS

| | | | |
|---|---|---|---|
| 4,310,931 A | 1/1982 | Muller | |
| 5,324,293 A * | 6/1994 | Rehmann | A61B 17/1659 606/85 |
| 5,665,118 A | 9/1997 | LaSalle et al. | |
| 5,800,555 A | 9/1998 | Gray | |
| 5,849,015 A | 12/1998 | Haywood et al. | |
| 5,910,171 A | 6/1999 | Kummer et al. | |
| 6,102,953 A | 8/2000 | Huebner | |
| 6,165,224 A * | 12/2000 | Tornier | A61F 2/389 606/86 R |
| 6,168,627 B1 | 1/2001 | Huebner | |
| 6,171,341 B1 | 1/2001 | Boileau et al. | |
| 6,187,012 B1 | 2/2001 | Masini | |
| 6,197,062 B1 | 3/2001 | Fenlin | |
| D440,630 S | 4/2001 | Gottwald | |
| 6,228,119 B1 | 5/2001 | Ondrla et al. | |
| 6,334,874 B1 * | 1/2002 | Tornier | A61F 2/4014 623/19.14 |
| 6,436,147 B1 | 8/2002 | Zweymuller | |
| 6,468,314 B2 | 10/2002 | Schwartz et al. | |
| 6,494,913 B1 | 12/2002 | Huebner | |
| 6,530,957 B1 | 3/2003 | Jack | |
| 6,648,894 B2 | 11/2003 | Abdelgany et al. | |
| 6,679,916 B1 | 1/2004 | Frankle et al. | |
| 6,899,736 B1 | 5/2005 | Rauscher et al. | |
| 6,989,034 B2 | 1/2006 | Hammer | |
| 7,001,389 B1 | 2/2006 | Navarro et al. | |
| 7,011,686 B2 | 3/2006 | Ball et al. | |
| 7,135,044 B2 | 11/2006 | Bassik | |
| 7,166,132 B2 | 1/2007 | Callaway et al. | |
| 7,175,663 B1 | 2/2007 | Stone | |
| 7,309,360 B2 | 12/2007 | Tornier et al. | |
| 7,445,638 B2 | 11/2008 | Benguin et al. | |
| 7,802,503 B2 | 9/2010 | Couvillion et al. | |
| 8,231,684 B2 | 7/2012 | Mutchler et al. | |
| 8,357,204 B2 | 1/2013 | Ragbir | |
| 8,512,410 B2 * | 8/2013 | Metcalfe | A61F 2/40 623/19.14 |
| 8,579,984 B2 | 11/2013 | Borowsky | |
| 8,663,333 B2 | 3/2014 | Metcalfe et al. | |
| 8,906,102 B2 | 12/2014 | Viscardi et al. | |
| 8,992,623 B2 * | 3/2015 | Hopkins | A61F 2/4003 623/23.12 |
| D744,612 S | 12/2015 | Peterson et al. | |
| 9,283,075 B2 | 3/2016 | Wiley et al. | |
| D757,252 S | 5/2016 | Von Moger et al. | |
| 9,498,344 B2 | 11/2016 | Hodorek et al. | |
| 9,566,162 B2 | 2/2017 | Isch | |
| 9,844,439 B2 | 12/2017 | Katrana et al. | |
| 10,034,759 B2 | 7/2018 | Deransart et al. | |
| 10,433,967 B2 | 10/2019 | Deransart et al. | |
| 11,173,037 B2 | 11/2021 | Deransart et al. | |
| D938,590 S | 12/2021 | Wolfe et al. | |
| 11,229,522 B2 | 1/2022 | Nerot et al. | |
| 2001/0010023 A1 | 7/2001 | Schwartz et al. | |
| 2001/0011193 A1 | 8/2001 | Nogarin | |
| 2001/0041940 A1 | 11/2001 | Pearl | |
| 2002/0151982 A1 | 10/2002 | Masini | |
| 2003/0028253 A1 | 2/2003 | Stone et al. | |
| 2003/0097183 A1 | 5/2003 | Rauscher et al. | |
| 2003/0171816 A1 | 9/2003 | Grant et al. | |
| 2004/0002765 A1 | 1/2004 | Maroney et al. | |
| 2004/0064190 A1 | 4/2004 | Ball et al. | |
| 2004/0153161 A1 | 8/2004 | Stone et al. | |
| 2005/0071014 A1 | 3/2005 | Barnett et al. | |
| 2006/0020344 A1 | 1/2006 | Shultz et al. | |
| 2006/0069445 A1 | 3/2006 | Ondrla et al. | |
| 2006/0276905 A1 | 12/2006 | Calamel | |
| 2007/0162140 A1 | 7/2007 | McDevitt | |
| 2007/0173945 A1 | 7/2007 | Wiley et al. | |
| 2007/0179624 A1 | 8/2007 | Stone et al. | |
| 2007/0225726 A1 | 9/2007 | Dye et al. | |
| 2007/0225821 A1 | 9/2007 | Reubelt et al. | |
| 2007/0244562 A1 | 10/2007 | Roche et al. | |
| 2008/0039860 A1 | 2/2008 | Trudeau | |
| 2008/0183297 A1 | 7/2008 | Boileau et al. | |
| 2008/0228281 A1 | 9/2008 | Forrer et al. | |
| 2009/0182336 A1 | 7/2009 | Brenzel et al. | |
| 2009/0210065 A1 | 8/2009 | Nerot et al. | |
| 2009/0265010 A1 | 10/2009 | Angibaud et al. | |
| 2009/0270865 A1 | 10/2009 | Poncet et al. | |
| 2009/0281630 A1 | 11/2009 | Delince et al. | |
| 2010/0049327 A1 | 2/2010 | Isch et al. | |
| 2010/0076572 A1 | 3/2010 | Jamali | |
| 2010/0094292 A1 | 4/2010 | Parrott | |
| 2010/0114326 A1 | 5/2010 | Winslow et al. | |
| 2010/0125336 A1 | 5/2010 | Johnson et al. | |
| 2010/0249797 A1 | 9/2010 | Trudeau et al. | |
| 2011/0029089 A1 | 2/2011 | Giuliani et al. | |
| 2011/0046625 A1 | 2/2011 | Boileau et al. | |
| 2011/0060417 A1 | 3/2011 | Simmen et al. | |
| 2011/0118846 A1 | 5/2011 | Katrana et al. | |
| 2011/0125285 A1 | 5/2011 | Ragbir | |
| 2012/0143204 A1 | 6/2012 | Blaycock et al. | |
| 2012/0209394 A1 | 8/2012 | Bojarski et al. | |
| 2012/0245646 A1 | 9/2012 | Gustilo et al. | |
| 2012/0253350 A1 | 10/2012 | Anthony et al. | |
| 2012/0253467 A1 | 10/2012 | Frankle | |
| 2013/0006369 A1 | 1/2013 | Wiley et al. | |
| 2013/0090736 A1 | 4/2013 | Katrana et al. | |
| 2013/0145609 A1 | 6/2013 | Sperling | |
| 2013/0197652 A1 | 8/2013 | Ekelund et al. | |
| 2013/0289738 A1 | 10/2013 | Humphrey | |
| 2013/0304228 A1 | 11/2013 | Phipps | |
| 2013/0325134 A1 | 12/2013 | Viscardi et al. | |
| 2014/0324185 A1 | 10/2014 | Bickley et al. | |
| 2015/0265411 A1 | 9/2015 | Deransart et al. | |
| 2016/0310176 A1 | 10/2016 | Van Dyke et al. | |
| 2016/0361173 A1 | 12/2016 | Reubelt et al. | |
| 2017/0049573 A1 | 2/2017 | Hodorek et al. | |
| 2017/0143494 A1 | 5/2017 | Mahfouz | |
| 2017/0273800 A1 | 9/2017 | Emerick et al. | |
| 2017/0304063 A1 | 10/2017 | Hatzidakis et al. | |
| 2017/0030449 A1 | 11/2017 | Deransart et al. | |
| 2018/0280152 A1 | 10/2018 | Mutchler et al. | |
| 2018/0325687 A1 | 11/2018 | Deransart et al. | |
| 2020/0289276 A1 | 9/2020 | Lefebvre et al. | |

FOREIGN PATENT DOCUMENTS

| | | |
|---|---|---|
| CN | 105213010 A | 1/2016 |
| CN | 209808650 U | 12/2018 |
| DE | 102 50 390 | 5/2004 |
| DE | 10 2005 003 097 | 7/2006 |
| DE | 102008010478 A1 | 8/2009 |
| EP | 0898946 A1 | 3/1999 |
| EP | 0927548 A2 | 7/1999 |
| EP | 1093777 | 4/2001 |
| EP | 1402854 A2 | 3/2004 |
| EP | 1472999 A1 | 3/2004 |
| EP | 1415621 A2 | 5/2004 |
| EP | 1 520 562 | 4/2005 |
| EP | 1265555 | 11/2005 |
| EP | 1520560 B1 | 10/2006 |

(56) References Cited

FOREIGN PATENT DOCUMENTS

| | | |
|---|---|---|
| EP | 1952788 | 8/2008 |
| EP | 1549258 B1 | 4/2011 |
| EP | 1048274 | 9/2012 |
| EP | 2 604 227 | 6/2013 |
| EP | 2604225 A1 | 6/2013 |
| FR | 2652498 A1 | 4/1991 |
| FR | 2 758 256 | 7/1998 |
| FR | 2773469 A1 | 7/1999 |
| FR | 2 932 678 | 12/2011 |
| JP | 2008528161 A | 7/2008 |
| JP | 2012143562 A | 8/2012 |
| WO | WO 93/09733 A1 | 5/1993 |
| WO | WO 96/17553 | 6/1996 |
| WO | WO 2004/080331 | 9/2004 |
| WO | 2006079895 A1 | 8/2006 |
| WO | WO 2007/084939 | 7/2007 |
| WO | WO 2007/082925 | 10/2007 |
| WO | 2007124607 A1 | 11/2007 |
| WO | WO 2008/000928 | 1/2008 |
| WO | WO 2008/050091 | 5/2008 |
| WO | 2008067400 A2 | 6/2008 |
| WO | WO 2008/109751 | 9/2008 |
| WO | WO 2013/064569 | 5/2013 |
| WO | 2014005644 A1 | 1/2014 |
| WO | WO 2014/067961 | 5/2014 |
| WO | WO 2014/178706 | 11/2014 |
| WO | WO 2015/112307 | 7/2015 |
| WO | WO 2016/094739 | 6/2016 |
| WO | WO 2017/184792 | 10/2017 |

OTHER PUBLICATIONS

Wright Media, "Tornier Aequalis Reversed FX", first available May 19, 2016. (https://www.wrightemedia.com/ProductFiles/Files/PDFs/ CAW-1146_EN_LR_LE.pdf) (Year: 2016), 6 pages.
Arthrex, "Univers Revers Shoulder System", first available Apr. 24, 2019. (https://www.arthrex.com/resources/surgical-technique-guide/ qkv6M00_50qt2QFBx1PKnA/univers-revers-shoulder-system) (Year: 2019).
Non-Final Office Action issued in connection with U.S. Appl. No. 17/149,527, filed Jan. 3, 2024, 17 pages.
International Search Report and Written Opinion issued in connection with International Patent Application No. PCT/US2022/070304, May 17, 2022, 15 pages.
Extended European Search Report issued in connection with European Patent Application No. 23214740.9, 7 pages, Apr. 29, 2024.
Non-Final Office Action issued in connection with U.S. Appl. No. 16/910,663, filed Jan. 16, 2024, 8 pages.
Extended European Search Report issued in connection with European Patent Application No. 22772355.8, Dec. 9, 2024, 7 pages.
First Office Action issued in connection with Japanese Patent Application No. 2022-183335, Aug. 15, 2023, 3 pages.
Communication issued in European Patent Application No. 18837131.4, Jul. 13, 2022, 6 pages.
First Office Action issued in connection with Japanese Patent Application No. 2021-097158, Jun. 14, 2022, 4 pages.
Non-Final Office Action issued in connection with U.S. Appl. No. 16/717,339, filed Jul. 18, 2022, 15 pages.
First Examination Report issued in connection with Australian Patent Application No. 2020204546, Oct. 21, 2021, 9 pages.
Non-Final Office Action issued in connection with U.S. Appl. No. 17/215,242, filed Feb. 1, 2024, 7 pages.
Final Rejection issued in connection with U.S. Appl. No. 16/717,339, Oct. 13, 202, 28 pages.
First Office Action issued in connection with Chinese Patent Application No. 201910099418.5, Feb. 7, 2024, 14 pages.
Non-Final Office Action issued in connection with U.S. Appl. No. 17/227,971, filed Feb. 16, 2024, 17 pages.
Extended European Search Report issued in connection with European Patent Application No. 23210681.5, Feb. 12, 2024, 9 pages.
International Preliminary Report on Patentability issued in connection with International Patent Application No. PCT/US2022/070304, Sep. 28, 2023, 11 pages.
Aston® Medical, "Operative Technique—Duocentric Expert Reversed,Total Shoulder Prosthesis".
Biomet Orthopedics, "Comprehensive® Shoulder System, Surgical Technique", 2007.
Delta, Delta CTA Reverse Shoulder Prosthesis, Surgical Technique, DePuy a Johnson & Johnson company, 2004.
Depuy, "GlobalTM Fx Shoulder Fracture System, Surgical Technique", 1999.
Depuy Synthes, "Global® UNITE Platform Shoulder System, Product Rationale & Surgical Technique", 2013.
DJO Surgical, "DJO Surgical Shoulder Solutions—Reaching Higher by Design", 2013.
Exactech, "Equinoxe Platform Shoulder System", 2014.
FH Orthopedics, "Arrow, Prothese d'epaule Universelle (Universal shoulder prosthesis)", Nov. 2009.
Integra, TitanTM Reverse Shoulder System, Surgical Technique, 2013.
JRI Orthopaedics, "Vaios® Shoulder System", 2011.
Levy et al., "Reverse Shoulder Prosthesis for Acute Four-Part Fracture: Tuberosity Fixation Using a Horseshoe Graft", J Orthop Trauma, vol. 25, No. 5, May 2011.
Lima Corporate, "SMR System, Surgical Technique".
Mathys European Orthopaedics, "Affinis® Fracture Affinis® Fracture Inverse, Technique operatoire".
Stryker Orthopaedics, "ReUnion Fracture System Surgical Protocol", 2007.
Tornier, "Aequalis Ascend Flex Convertible Shoulder System", Feb. 8, 2016.
Tornier, "Aequalis-Fracture Shoulder Prosthesis".
Tornier, "Aequalis® Reversed Adapter, Surgical Technique Shoulder Revision System".
Tornier, "Aequalis® Reversed Fracture, Surgical Teachnique Reversed Shoulder Prosthesis".
Zimmer, "Anatomical ShoulderTM Fracture System, Surgical Technique", 2010.
Zimmer®, "Trabecular MetalTM Humeral Stem—Enabling fracture healing", 2009.
Search Report and Written Opinion issued in French Application No. 14 62206, dated Jul. 31, 2015, in 7 pages.
International Search Report and Written Opinion for PCT/US15/65126 mailed Apr. 28, 2016 in 18 pages.
Office Action issued in connection with Korean Patent Application No. 10-2021-7004528, May 6, 2021, 16 pages.
Non-Final Office Action issued in connection with U.S. Appl. No. 17/590,234, filed May 20, 2022, 10 pages.

* cited by examiner

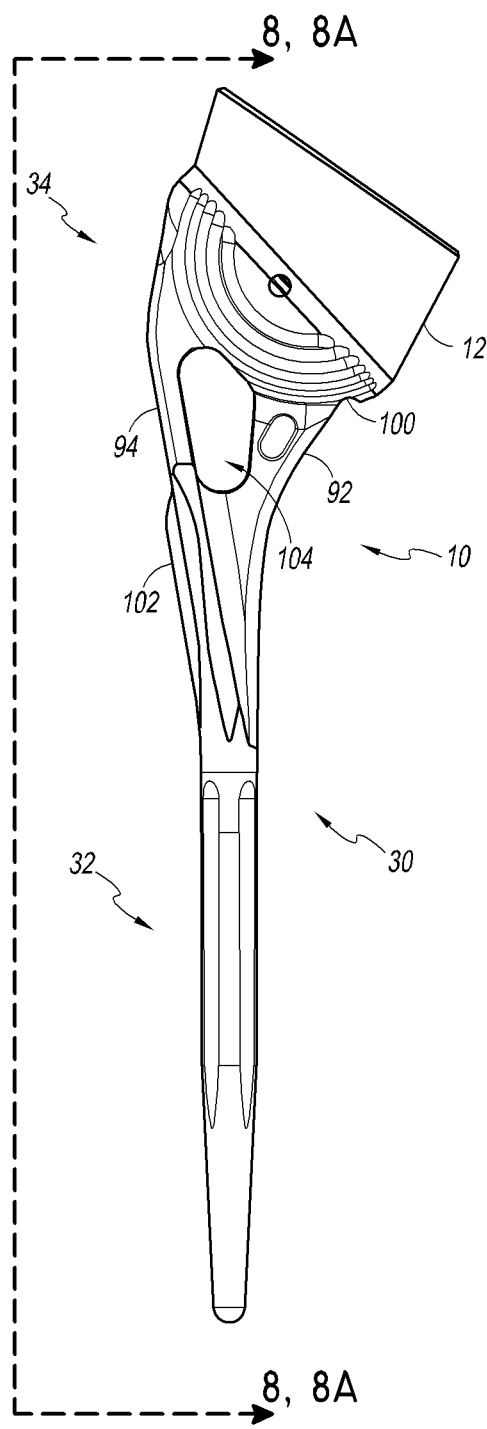
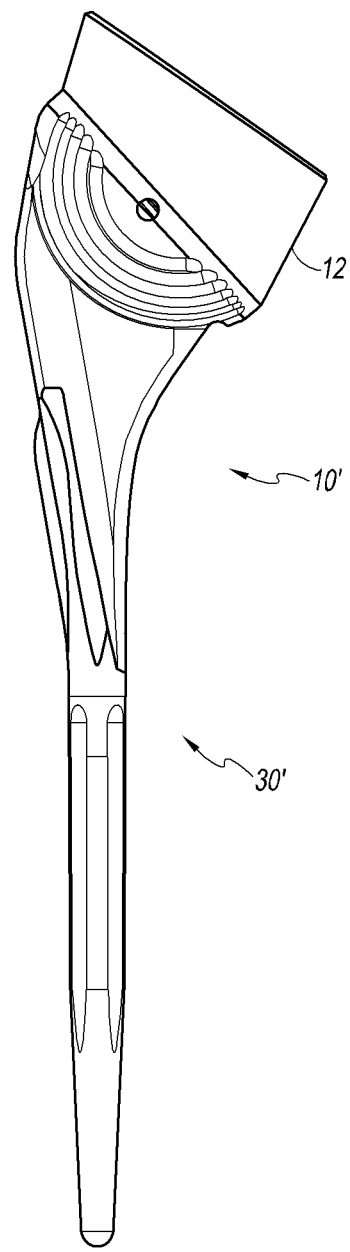
FIG. 1A
FIG. 1B

CONVERTIBLE STEM/FRACTURE STEM

CROSS-REFERENCE TO RELATED APPLICATIONS

This application is a continuation of copending U.S. application Ser. No. 16/554,013, filed on Aug. 28, 2019, which is a division of U.S. application Ser. No. 15/532,035, filed on May 31, 2017, now U.S. Pat. No. 10,433,967, filed as application No. PCT/US2015/065126 on Dec. 10, 2015, the contents of which are incorporated by reference herein.

FIELD OF DISCLOSURE

The present application relates to apparatuses and methods for reverse and anatomic shoulder prostheses.

BACKGROUND

Arthroplasty is the standard of care for the treatment of shoulder joint arthritis. A typical anatomical shoulder joint replacement attempts to mimic anatomic conditions. For example, a metallic humeral stem and a humeral head replacement are attached to the humerus of the arm and replace the humeral side of the arthritic shoulder joint. Such humeral head replacement can articulate with the native glenoid socket or with an opposing glenoid resurfacing device.

For more severe cases of shoulder arthritis, the standard treatment is a reverse reconstruction, which includes reversing the kinematics of the shoulder joint. A reverse shoulder prosthesis can be provided by securing a semi-spherical device (sometimes called a glenoid sphere) to the glenoid and implanting a humeral stem with a cavity capable of receiving the glenoid sphere.

As patient disease may progress after anatomic treatment, revision surgery may be necessary to perform a reverse reconstruction of the shoulder. In the known art, the change in the type of prosthesis is addressed either below the plane of resection or above the plane of resection. In prosthesis that are converted from anatomic to reverse by a modularity below the plane of resection, removal of anatomic devices that have integrated into the patient's bony anatomy proves to be difficult for the surgeon, and could potentially cause excessive patient bone loss. One advantage of such conversion is that the reverse insert could partially reside below the resection plane and therefore reduce the distance between the cavity and the lateral contour of the humerus. Such position has proven to be beneficial to a reversed kinematics. In contrary, in prosthesis that are converted from anatomic to reversed above the plane of resection thanks to an adaptor, reverse kinematic is altered as the position of the cavity is further push out of the humerus by the addition of the adaptor above the resection plane. Such construct are typically made of 3 components that present an extra modularity in comparison to 2 components construct and could potentially cause disassembly or breakage of the construct. One possibility to limit the alteration of the kinematics and limit the modularity is to inverse the bearing surface material by having a harder cavity within the humerus and a softer semi-spherical device secured to the glenoid. But the proven clinical design and preferred embodiment is usually that the cavity is softer than the semi-spherical device.

In cases of displaced or dislocated 3- and 4-part proximal humeral fractures, the proximal humerus also needs to be reconstructed. Although hemi-arthroplasty procedures may be used for the treatment of such displaced fractures, the functional outcomes of these procedures are often reported as poor and unpredictable.

SUMMARY

A convertible prosthesis that can be converted from an anatomic replacement to a reverse reconstruction without removal of parts integrated into the patient's bony anatomy is highly desirable. For improved patient outcomes, such a convertible prosthesis should respect the biomechanics of a true anatomic replacement while also performing well when converted into a reverse reconstruction. In some cases, it may also be desirable for the convertible prosthesis to be configured for use in a humeral fracture repair procedure.

The aim of the present invention is to provide efficient surgical means that are appropriate to this problematics.

To that end, the invention relates to a kit for a shoulder prosthesis, comprising:
  a humeral anchor comprising a proximal portion and a distal portion, the proximal portion including a proximal face, the proximal face comprising a hole and a cavity that is distinct from the hole;
  a reverse insert having a proximal portion and a distal portion, the proximal portion including a concave surface configured to receive a glenosphere and the distal portion comprising a protrusion, wherein the reverse insert is configured to directly couple to the cavity of the proximal face; and
  an anatomical insert having a proximal portion including a convex surface and a distal portion including a protrusion, wherein the anatomical insert is configured to directly couple to the hole of the proximal face.

More generally, according to some embodiments of the present disclosure, a convertible prosthesis system includes a humeral anchor, an anatomic or humeral head insert, and a reverse insert. The system advantageously has a 2-part construction for each of the anatomic configuration and the reverse configuration, with one of the parts common to both configurations. The modularity of the system is advantageously located at a humeral resection plane. In some embodiments, the humeral anchor is a fracture stem configured for use in a humeral fracture repair procedure.

In some embodiments, the anatomical insert and the reverse insert are made out of different materials but each being monolithic. In some embodiments, the reverse insert resides partially below the resection plane.

According to additional advantageous features of the set according to the invention, considered alone or according to all technically possible combinations:
  the anatomical insert is configured to rotationally engage the proximal face;
  the protrusion of the anatomical insert is configured to rotationally engage the hole of the proximal face;
  the humeral anchor is a fracture stem;
  the humeral anchor comprises a stem comprising a metaphyseal portion comprising a medial arm and first and second lateral arms extending between and connecting the distal portion and the proximal portion of the stem;
  the kit further comprises a bone graft;
  the bone graft is shaped to be received thereon the stem;
  the bone graft is selected from the group consisting of bone, stem cells, ceramic, polymer and porous metal;
  the bone graft is selected from the group consisting of an allograft and autograft;
  the proximal portion of the humeral anchor comprises a spherical portion;

the proximal face further comprises a groove extending around an inner periphery of the cavity;

the protrusion of the reverse insert further comprises a locking member configured to engage the groove of the proximal face;

the proximal face further comprises a ridge defining an inner periphery of the cavity smaller than an outer periphery of the protrusion of the distal portion of the reverse insert, whereby an interference fit is provided between the protrusion of the distal portion of the reverse insert and the cavity when the reverse insert is engaged with the humeral anchor;

an interference fit is provided between the protrusion of the distal portion of the reverse insert and the cavity when the reverse insert is engaged with the humeral anchor;

a periphery of the cavity is spaced from and surrounds the hole configured to receive the protrusion of the anatomical insert;

the hole configured to receive the protrusion of the anatomical insert is at least partially formed in a raised portion of the proximal face, the raised portion extending proximally from a base of the cavity;

a distal end of the protrusion of the reverse insert comprises a recess configured to engage the raised portion of the stem face;

an interface between the raised portion of the proximal face and the recess of the reverse insert is configured to resist rotation between the reverse insert and the humeral anchor;

a central axis extending proximally and distally through the hole is offset from a central axis extending proximally and distally through the cavity;

the reverse insert is configured to directly couple to the proximal face via a snap-fit;

the humeral anchor comprises a unitary body;

the distal portion of the humeral anchor comprises a taper;

the humeral anchor comprises a base member comprising a distal end configured to be embedded in bone and a proximal end to be disposed at a bone surface, the base member having a plurality of spaced apart arms and a concave member comprising the hole projecting from the proximal end toward the distal end; and an anchor component comprising the proximal face and having a distal portion advanceable into the base member to a position disposed within the arms, the distal portion of the anchor component configured to project circumferentially into a space between the arms, the distal portion of the anchor component being exposed between the arms when the anchor component is advanced into the base member; wherein the cavity is defined at least in part by the proximal face of the anchor component;

the proximal face of the anchor component comprises an aperture configured to be advanced over a proximal portion of the concave member;

the proximal face comprises a driver interface disposed thereon outward of the aperture;

the distal portion of the anchor component comprises a cylindrical sleeve and a thread projecting laterally therefrom;

the kit further comprises a locking device disposed between the anchor component and the base member to prevent disengagement of the anchor component from the base member.

The invention further relates to a method of using the kit as defined above, this method comprising selecting intraoperatively to implant the reverse shoulder insert or the anatomical shoulder insert.

The invention further relates to a stem for a shoulder prosthesis is provided that includes a distal shaft portion, a proximal portion, and a metaphyseal portion. The distal shaft portion is adapted to be anchored in a medullary canal of a humerus. The proximal portion includes a stem face. The stem face includes a first engagement feature configured to directly couple with a reverse insert and a second engagement feature configured to couple with an anatomical insert. Further, the first engagement feature is distinct from the second engagement feature. The metaphyseal portion includes a medial portion and first and second lateral arms extending between and connecting the shaft portion and the proximal portion.

In some variations of the stem, the second engagement feature is configured to directly couple with the anatomical insert. In some embodiments, the stem further includes a notch configured to engage a suture. The stem can further include a fin protruding from a lateral side of the shaft portion and extending from a proximal portion of the shaft portion distally along a portion of a length of the shaft portion. In some embodiments, the medial portion includes an arm having a lateral edge, the first and second lateral arms have medial edges, and a fenestration is defined between the lateral edge of the medial arm and the medial edges of the first and second lateral arms. In some embodiments, the first lateral arm has a first inner edge, the second lateral arm has a second inner edge, the first and second inner edges face one another, and a gap is formed between the first and second inner edges. In some such embodiments, the gap extends from a proximal end of the shaft portion to a distal end of the proximal portion. In that case, the stem may further comprises a bone graft shaped to be received thereon the gap from lateral wherein the graft fill the fenestration and contact the lateral edge of the medial arm. If any, the graft extends laterally above the lateral edges of the first and second lateral arms. In variation, the graft extends laterally from the gap to cover the lateral edge and the outer edge, opposite to the inner edge, of the first lateral arm and to cover the lateral edge and the outer edge, opposite to the inner edge, of the second lateral arm.

The invention further relates to a humeral anchor for a shoulder prosthesis is provided. The humeral anchor has a distal portion and a proximal portion. The distal portion is configured to be anchored in a proximal region of a humerus. The proximal portion includes a proximal face. The proximal face includes an engagement feature configured to directly couple to a reverse should insert having a concave proximal portion. The proximal face is also configured to directly couple with an anatomical shoulder insert having a convex proximal portion.

In some variations, a kit including the humeral anchor further includes a reverse insert that has a proximal portion that includes a concave surface configured to engage a glenosphere and a distal portion that is configured to directly attach to the engagement feature of the proximal face. In some embodiments, the proximal face further includes a cavity having an inner dimension, the distal portion of the reverse insert has an outer dimension, and an interference fit is provided between the distal portion of the reverse insert and the cavity when the reverse insert is engaged with the humeral anchor. In some embodiments, the kit further includes an anatomical insert that has a proximal portion including a convex surface and a distal portion that is configured to couple to the proximal face.

In some embodiments, the humeral anchor includes: a base member comprising a distal end configured to be embedded in bone and a proximal end to be disposed at a bone surface, the base member having a plurality of spaced apart arms and an anchor component having a proximal end and a distal portion advanceable into the base member to a position disposed within the arms, and the distal portion of the anchor component comprises threads configured to project circumferentially into a space between the arms, the threads being exposed between the arms when the anchor component is advanced into the base member. In some embodiments, the humeral anchor further includes a concave member comprising a hole configured to receive a distal shaft of an anatomical shoulder insert. In some embodiments, the anchor component at least partially defines a cavity configured to engage a reverse shoulder insert.

The invention further relates to a method for shoulder surgery is provided. In this method, a humeral anchor is provided. The humeral anchor includes a distal portion and a proximal portion. The proximal portion includes a proximal face that is configured to directly couple to a reverse shoulder insert and an anatomical shoulder insert. A surgeon or other user chooses intra-operatively to implant the reverse shoulder insert or the anatomical shoulder insert. The surgeon or other user implants a two-component shoulder system that is selected from the group consisting of a humeral anchor directly attached to the reverse shoulder insert and a humeral anchor directly attached to the anatomical shoulder insert.

The invention further relates to a method for shoulder surgery is provided. In this method, a humeral anchor of a humeral component shoulder system is implanted at least partially in a proximal portion of a humerus. The humeral anchor is adapted to directly interface with a one-component reverse shoulder insert and an anatomical shoulder insert. A surgeon or other user chooses intra-operatively to implant a one-component reverse shoulder insert or an anatomical shoulder insert. The surgeon or other user directly couples the chosen insert to the humeral anchor.

The invention also relates to a method for shoulder surgery is provided. In this method, a humeral anchor is disposed at least partially in a proximal portion of a humerus. A surgeon or other user selects a reverse shoulder insert or an anatomical shoulder insert. The reverse shoulder insert includes a body with a concave articular surface on one side and an engagement structure projecting from a side of the body opposite the concave surface. The surgeon or other user implants the insert that has been chosen by directly coupling the chosen insert to the humeral anchor.

The invention further relates to a method for revision shoulder surgery is provided. In this method, an anatomical shoulder insert is removed from a humeral anchor implanted in a patient's humerus to expose a proximal face of the humeral anchor. A reverse shoulder insert is directly coupled to the proximal face.

The invention further relates to a kit for a shoulder prosthesis that includes a stem and a bone graft cutter. The stem includes a unitary body having a shaft portion configured to be anchored in a medullary canal of a humerus and a proximal portion. The proximal portion includes a stem face that includes an engagement feature configured to directly couple to a reverse shoulder insert having a concave proximal portion. The stem face is further configured to directly couple with an anatomical shoulder insert having a convex proximal portion.

In some variations, the bone graft cutter includes a drill guide and a cutting cap. In some such variations, the drill guide includes at least 4 holes provided at different angles. The cutting cap can be shaped to be received therein the drill guide. In some variations, the kit includes a drill, mallet, and/or bone graft. The bone graft can be shaped to be received thereon the stem. The bone graft can be selected from the group consisting of bone, stem cells, ceramic, polymer and porous metal. The bone graft can be selected from the group consisting of an allograft and autograft.

The invention further relates to a kit for a shoulder prosthesis is provided that includes a humeral anchor and an anchor holder. The humeral anchor includes a distal portion configured to be anchored in a proximal portion of a humerus and a proximal portion. The proximal portion includes a proximal face that includes an engagement feature configured to directly couple to a reverse shoulder insert having a concave proximal portion. The proximal face is further configured to directly couple with an anatomical shoulder insert having a convex proximal portion.

In some variations of this kit, the anchor holder is monolithic. The anchor holder can be deformable. In some variations, the anchor holder includes at least one compression feature configured to retain the engagement feature of the proximal face. The anchor holder can be in a snap-fit arrangement with the face. The anchor holder can be in an interference fit arrangement with the face.

In some embodiments, a kit for a shoulder prosthesis comprises:
 a humeral anchor comprising a proximal portion and a distal portion, the proximal portion including a proximal face;
 a reverse insert having a proximal portion and a distal portion, the proximal portion including a concave surface configured to receive a glenosphere and the distal portion comprising a protrusion; and
 an anatomical insert having a proximal portion including a convex surface and a distal portion including a protrusion;
 characterized in that the proximal face comprises a hole and a cavity that is distinct from the hole, the reverse insert is configured to directly couple to the cavity of the proximal face, and the anatomical insert is configured to directly couple to the hole of the proximal face.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

FIG. 1A is a side plan view of a reverse shoulder prosthesis;

FIG. 1B is a side plan view of another embodiment of a reverse shoulder prosthesis;

DETAILED DESCRIPTION

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Figures 2A, 2B:
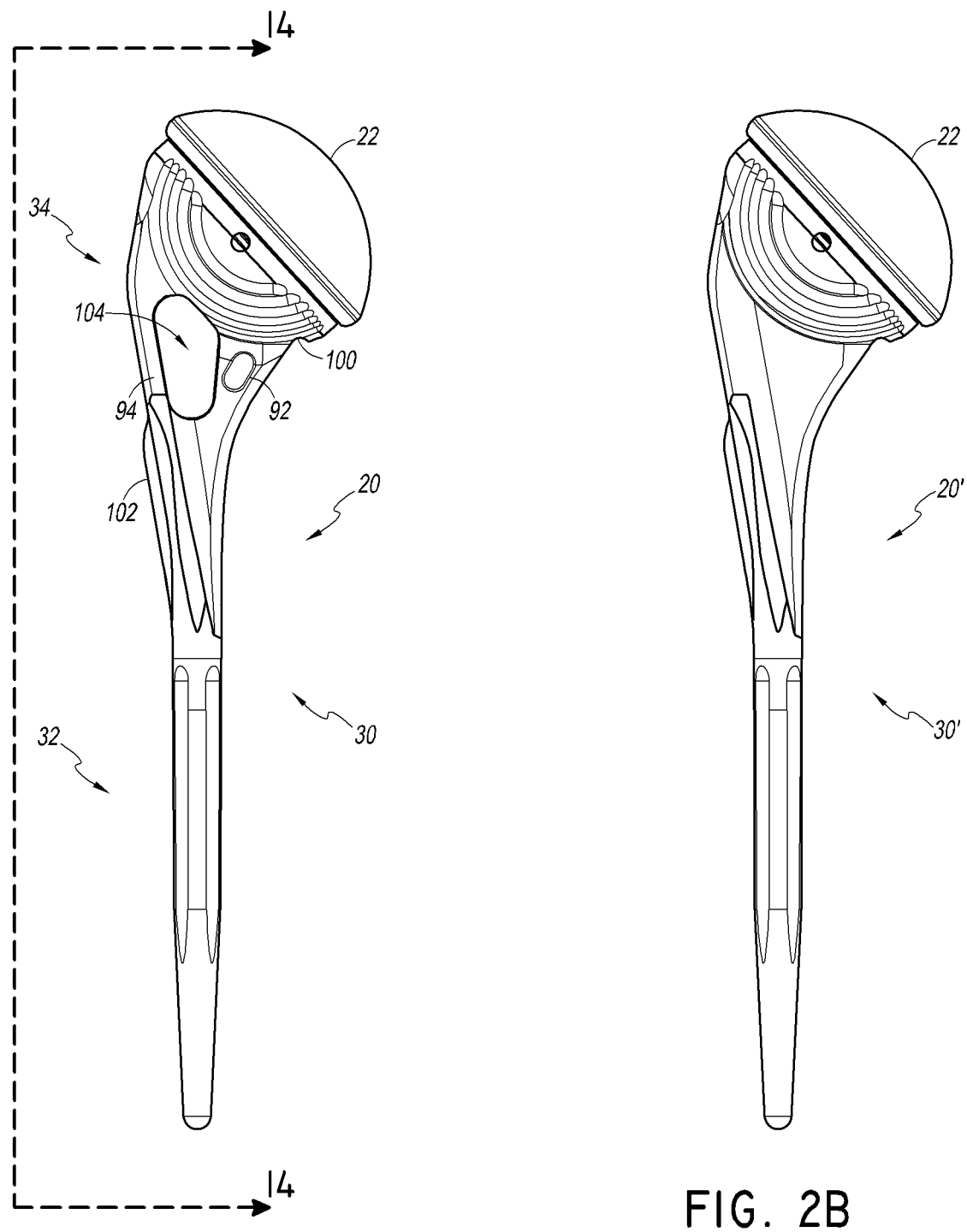
FIG. 2A is a side plan view of an anatomic shoulder prosthesis.
FIG. 2B is a side plan view of another embodiment of an anatomic shoulder prosthesis.

FIG. 1A illustrates a modular reverse shoulder prosthesis 10, and FIG. 2A illustrates a modular anatomic shoulder prosthesis 20, according to embodiments of the present disclosure. The reverse shoulder prosthesis 10 includes a stem 30 and a reverse insert 12. The stem 30 is one embodiment of a humeral anchor disclosed herein. In embodiments, the anatomic shoulder prosthesis 20 includes the same stem 30 and an anatomic insert or humeral head 22. FIG. 1B illustrates another example embodiment of a modular reverse shoulder prosthesis 10' including a stem 30' and reverse insert 12, and FIG. 2B illustrates another example embodiment of a modular anatomic shoulder prosthesis 20' including the same stem 30' and the anatomic insert or humeral head 22. The stem 30' is another embodiment of a humeral anchor disclosed herein. The stem 30, 30', anatomic insert 22, and reverse insert 12 can be made of various materials, for example, metal, such as titanium, a ceramic material, ultra-high molecular weight polyethylene (UHMWPE), or other materials, and may include bioactive coatings such as HA or vitamin E, each of which may be porous or non-porous. In one embodiment the reverse insert is monolithic and comprise one unique material softer than the one comprised in the anatomic insert. More specifically, the reverse insert may comprise UHMWPE.

Figure 23:
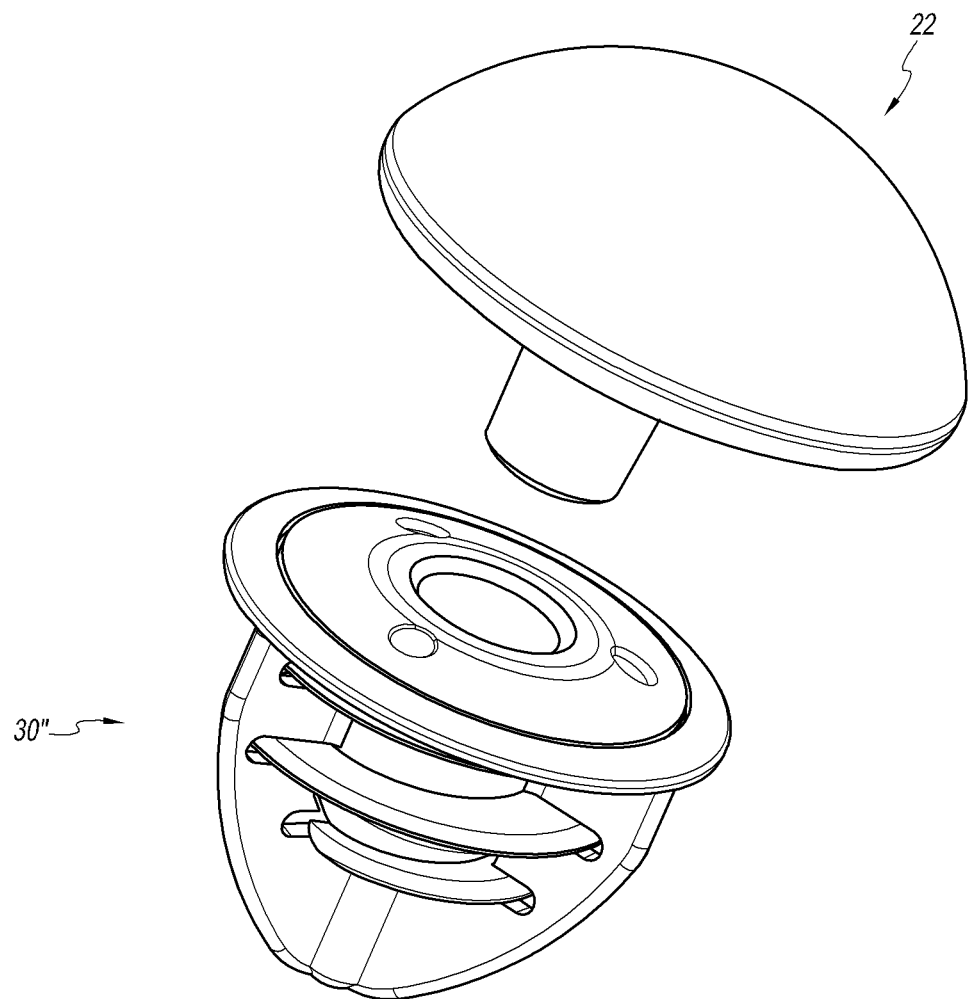
FIG. 23 illustrates a stemless anatomic shoulder prosthesis.

FIGS. 3-6 illustrate one embodiment of the stem 30 in greater detail. The stem 30 of FIGS. 1A and 2A is a fracture stem configured to be used in humeral fracture repair procedures as described herein. The stem 30' of FIGS. 1B and 2B is a non-fracture stem and therefore may not include all of the features of stem 30 described herein, but may include other features of the stem 30. The stem 30 is configured to be anchored in a medullary canal of a humerus of a patient. The stem 30 includes a shaft or distal portion 32 and a proximal portion 34. In some embodiments, the stem 30 is a unitary body. In some embodiments, a humeral anchor is provided that has a unitary body. In other words, the stem 30 is monolithic, and the distal portion 32 and proximal portion 34 are integrally formed. In some embodiments, the stem 30, the stem 30', and/or other humeral anchors herein can have a distal portion that includes a taper. For example, the shaft portion 32 can have a gradually tapered overall shape to better fit the humerus bone into which it is implanted. A length of the distal portion 32 of the stem 30, 30' can vary. In some embodiments, a modular reverse shoulder prosthesis and a modular anatomic shoulder prosthesis including various features as described herein can be stemless. In other words, the prosthesis need not include the shaft or distal portion 32. For example, FIG. 23 illustrates an example embodiment of a stemless anatomic shoulder prosthesis including a humeral anchor 30" and the anatomic insert 22. The humeral anchor 30" is another embodiment of a humeral anchor disclosed herein.

In some embodiments, the proximal portion 34 includes a spherical portion. For example, in the illustrated embodiment, the outer surface 35 of the proximal portion 34 is shaped generally as a half-sphere. A proximal end of the proximal portion 34 includes a stem face 36. The stem face 36 is one example of a proximal face as disclosed herein. The stem 30' may also have the features of the stem face 36. The humeral anchor 30" has a proximal portion that may include some or all of the features of the stem face 36. For example, the stem face 36 and the proximal face of the humeral anchor 30" can each have a hole for mounting an anatomic insert and a cavity for mounting a reverse insert, as discussed in greater detail below. The stem 30' of the reverse shoulder prosthesis 10' of FIG. 1B and the anatomic shoulder prosthesis 20' of FIG. 2B can include any or all of the features of the stem face 36 of stem 30 described and shown herein. A proximal end of the humeral anchor 30" of the stemless design shown in FIG. 23 can also include any or all of the features of the stem face 36 described and shown herein. A distal portion of the humeral anchor 30" can include a taper as discussed further below.

Figure 4A:
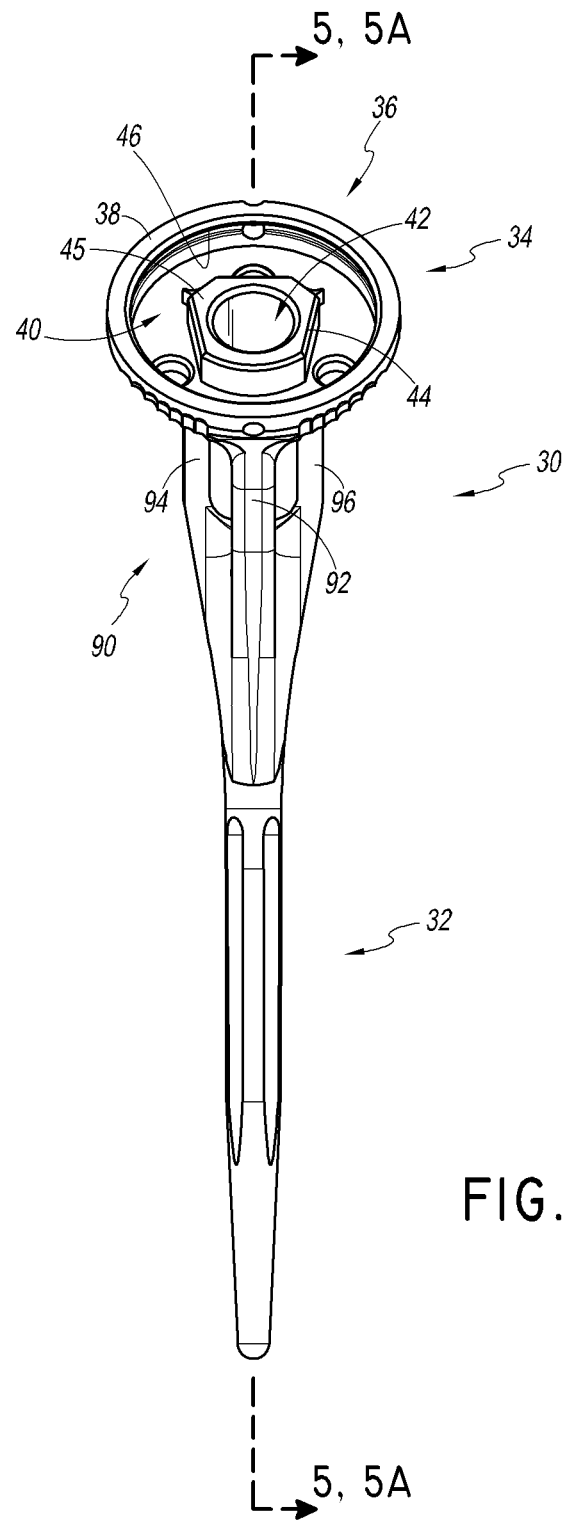
FIG. 4A is a first view of the stem of FIG. 3.
Figure 4B:
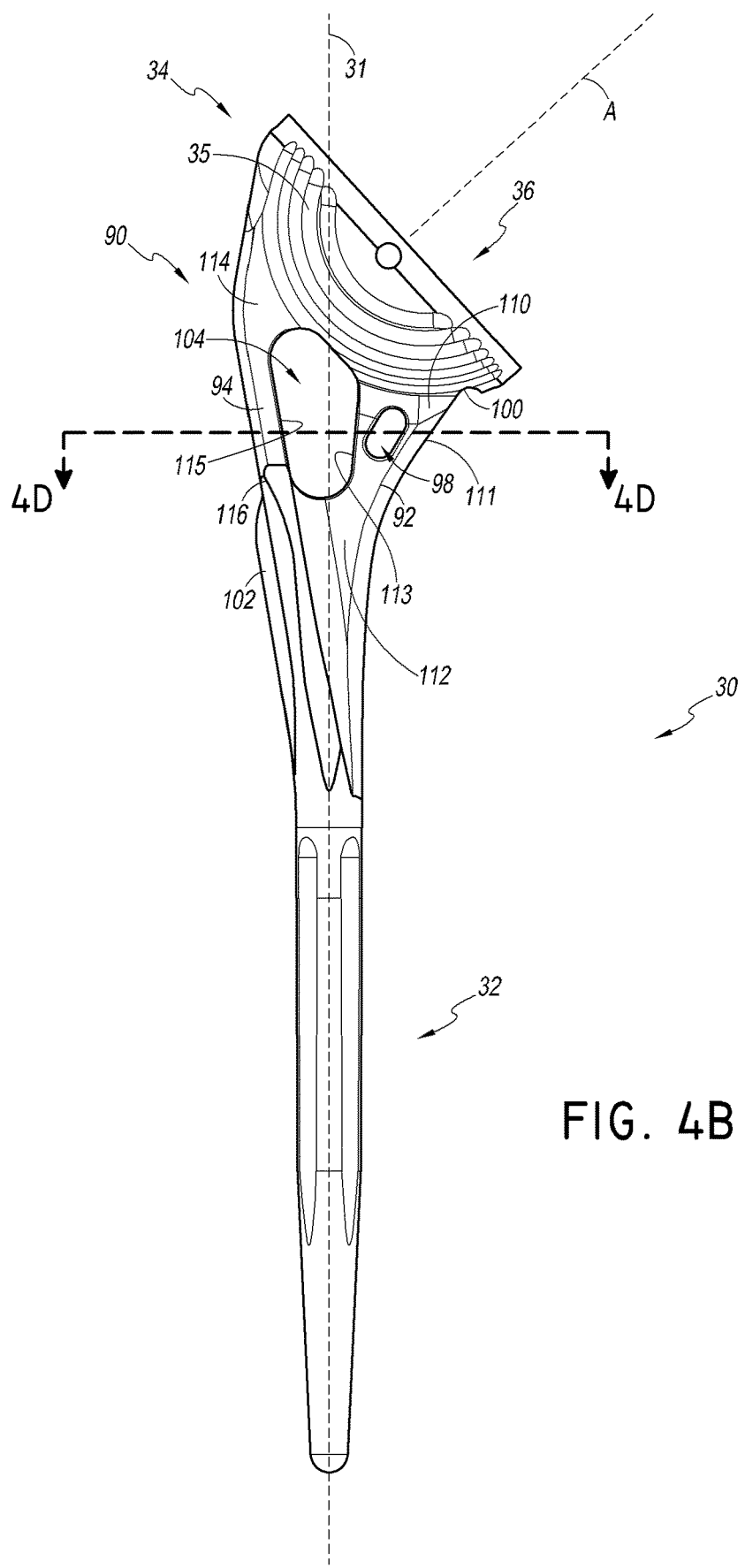
FIG. 4B is a second side view of the stem of FIG. 3.

The stem face 36 is oriented at an angle relative to a longitudinal stem axis 31, shown in FIG. 4B. An obtuse angle between an axis A (also shown in FIG. 4B) normal to the plane of the stem face 36 and the stem axis 31 can be in the range of about 120° to about 150°. For example, in the illustrated embodiment, the angle between the normal axis A and the stem axis 31 is about 132.5°. The angle can be selected to allow the stem 30 to provide desirable biomechanics when used in the anatomic shoulder prosthesis 20 as well as to perform well when used in the reverse shoulder prosthesis 10. Other angles are also possible, for example, 127.5°, 137.5°, and other angles. The reverse insert 12 can also be made with various inclination angles as described in greater detail herein to produce a reverse shoulder prosthesis 10 having a variety of overall angles. For example, the overall angle of the prosthesis 10 can be in the range of 130° to 155°. The angle of the stem face 36 can be selected based on pre-operative imaging of the patient's humeral bone. The inclination angle and thickness of the reverse insert 12 can be selected based on a numerical simulation of range of motion using virtual surgery. The inclination angle can be selected to achieve an optimized range of motion, which results in no or minimized contact between a medial side of the insert 12 and the scapula pillar in any movement (e.g., adduction, flexion-extension, internal and external rotation) and no or minimized limitation due to contact between the humerus and scapula during arm elevation.

Whereas some available shoulder prosthesis systems require an adapter or spacer to couple either or both of a reverse insert and an anatomic insert to a stem, the stem face 36 of the present disclosure advantageously is configured to couple or attach directly to either of the reverse insert 12 and the anatomic insert 22 without the need for a spacer, adapter, or the like. The stem face 36 includes a first engagement feature configured to directly couple with the reverse insert 12 and a second engagement feature configured to couple with the anatomic insert 22. In the illustrated embodiment, the first engagement feature includes a cavity 40 recessed from a peripheral rim 38 of the stem face 36, and the second engagement feature includes a hole or female tapered recess 42. The first engagement feature is distinct from the second engagement feature. More specifically, the cavity 40 is distinct from the hole or the female tapered recess 42. Having two engagement features offer several advantages. The first advantage is to adapt each engagement feature to the specific properties of the most suitable material for the reverse insert and to the specific properties of the most suitable material for the anatomic insert. In contrary, having only one engagement features only obliged to alter the material of one of the insert or to alter the engagement feature of one of the insert. Both of those alteration might cause unsatisfactory issues such as increased wear, disassembly, breakage and the like. The second advantage is to adapt the position of each engagement features to the most suitable position. For example, it is known in the prior art that the most suitable position for the cavity of the reverse insert is to partially reside below the resection plane while the most suitable position for the convexity of the anatomic insert is to reside above the resection plane.

Figure 6:
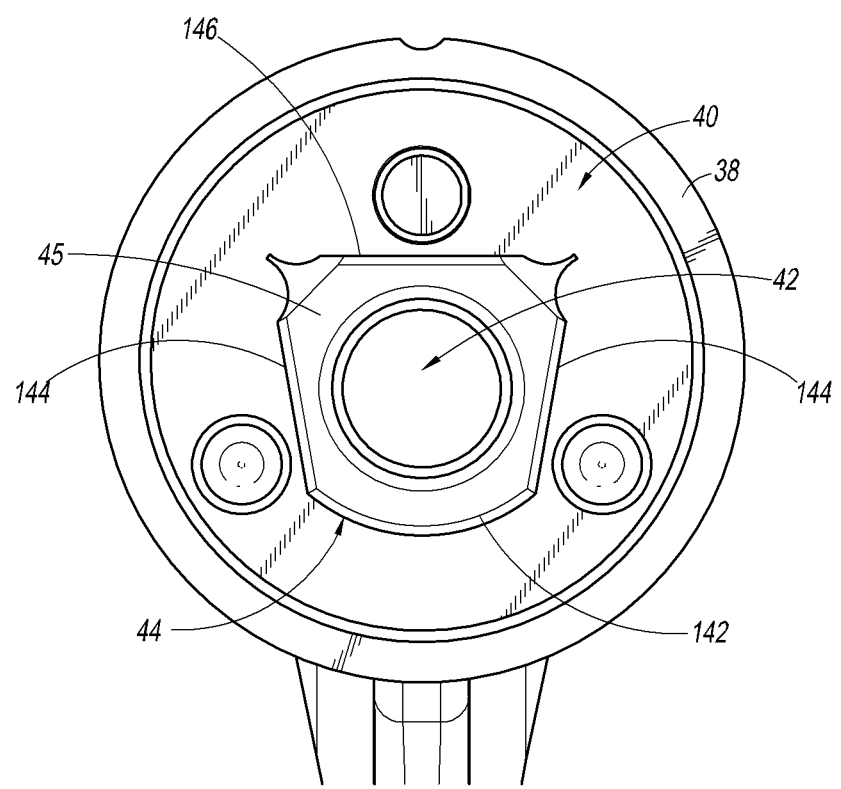
FIG. 6 is a plan view of one embodiment of a face of the stem of FIG. 3, the face being configured to couple with a reverse insert to form the reverse shoulder prosthesis of FIG. 1A and with an anatomic insert to form the anatomic shoulder prosthesis of FIG. 2A.

A periphery or sidewall 41 of the cavity 40 is radially spaced from and surrounds the hole 42. The outer periphery of the cavity 40 surrounded by the sidewall 41 can be circular or generally circular as shown, although other shapes and configurations are also possible. The stem face 36 can further include a groove 46 extending around an inner periphery or circumference of the cavity 40. As shown, the groove 46 is recessed in the sidewall 41 of the cavity 40 and therefore extends radially outwardly from the cavity 40. The hole 42 can be at least partially formed in a raised portion 44 of the stem face 36. The raised portion 44 extends proximally from a base 43 of the cavity 40. As shown, a proximal surface 45 of the raised portion 44 can be in the same plane or substantially the same plane as the peripheral rim 38. In the illustrated embodiment, the outer perimeter of the raised portion 44 has a non-circular and radially asymmetric shape. As shown in FIG. 6, in various embodiments the raised portion 44 has at least one flat peripheral edge. For example, the raised portion 44 can have a curved base 142, one or more angled sides 144 that angle outwardly from the curved base 142, and a straight top surface 146. Alternatively, in some embodiments where rotation of the reverse insert is desired, the raised portion 44 can have a shape that is circular or non-circular but rotationally symmetric. In some embodiments, the sidewall 41 of the cavity 40 can be non-circular but rotationally symmetric. For example, the sidewall 41 can have a rotationally symmetric cross-sectional shape similar to that of the metaphysis described in PCT Publication No. WO 2013/064569, the entirety of which is hereby incorporated by reference herein.

Figure 5:
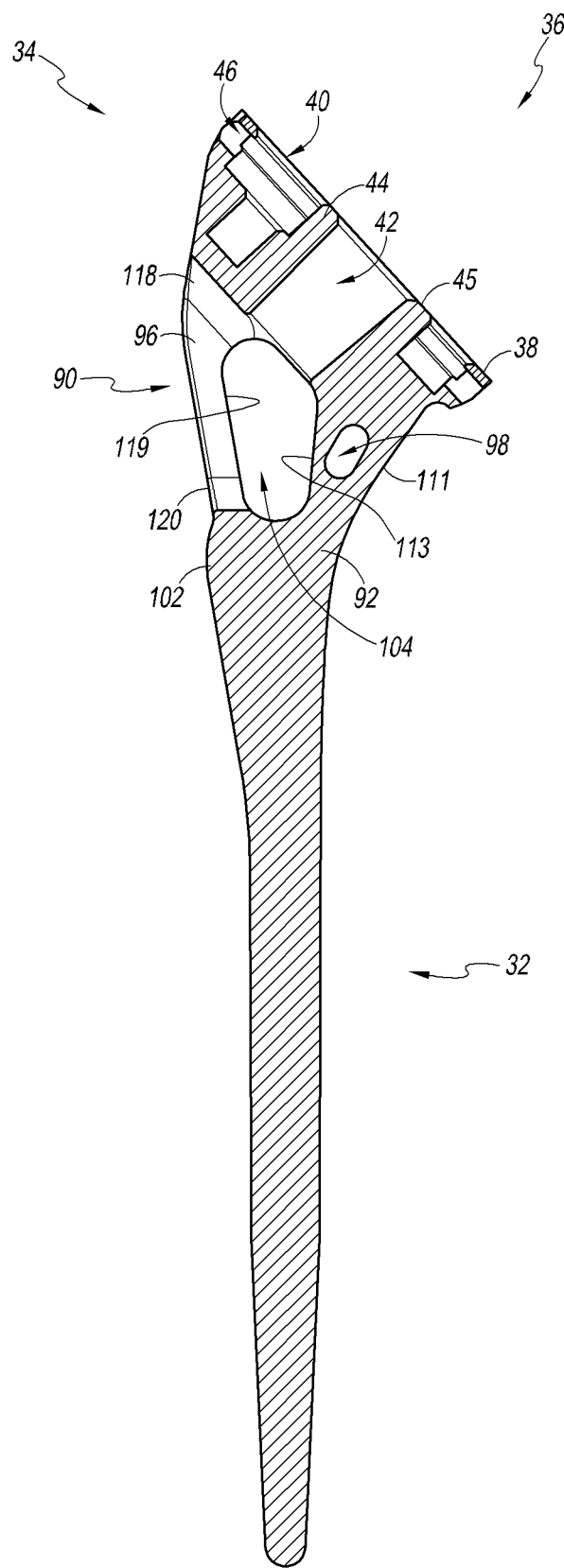
FIG. 5 is a cross-sectional view of the stem of FIG. 3 taken through the section plane 5-5 in FIG. 4A.
Figure 5A:
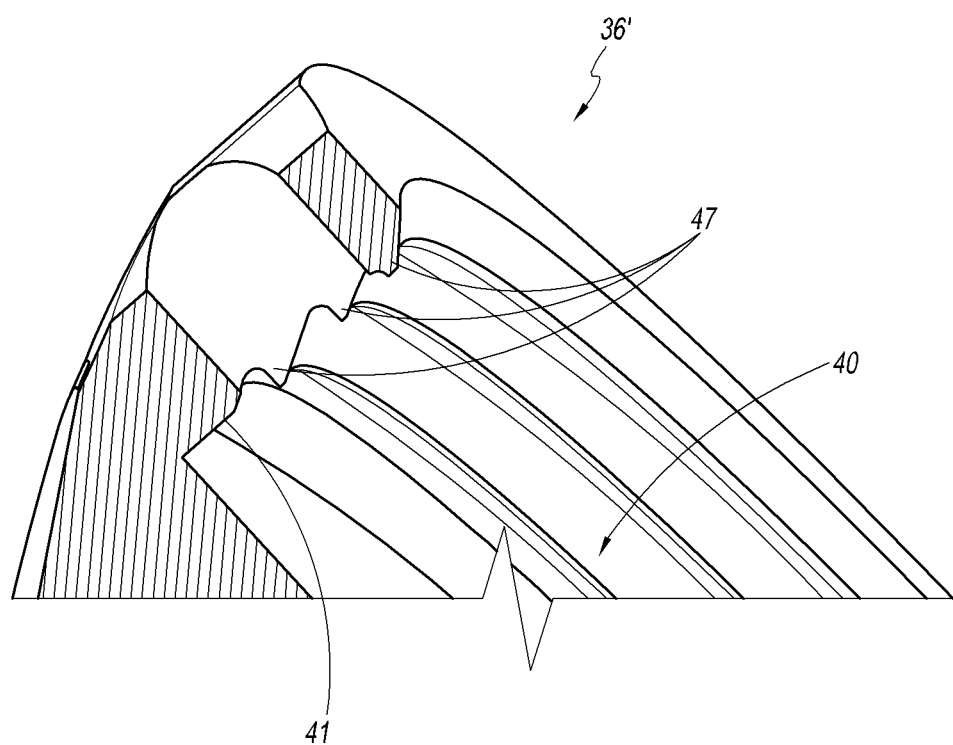
FIG. 5A is a detail cross-sectional view of a portion of another embodiment of a stem.

FIG. 5A illustrates an alternative embodiment of a stem face 36'. The stem face 36' is similar to the stem face 36 except as described differently below. The stem face 36' can be incorporated into any humoral anchor according to the present disclosure, including the stem 30, the stem 30', the humoral anchor 30", or the humoral anchor 200. As shown, the stem face 36' includes one or more ridges 47 extending radially inwardly into the cavity 40 from the sidewall 41. In the illustrated embodiment, the ridges 47 are integrally formed with the sidewall 41. In other words, the sidewall 41 and ridges 47 are monolithic. However, in other embodiments, the ridges 47 can be formed separately from and coupled, removably or permanently, to the sidewall 41. In the illustrated embodiment, the stem face 36' includes three ridges 47, although more or fewer ridges 47 are also possible. The ridges 47 (e.g., the peaks 47A or innermost points of the ridges 47) define an inner dimension of the cavity 40. In the illustrated embodiment, the ridges 47 are generally triangular. As shown, a distal surface of the ridge(s) 47 can extend perpendicular or generally perpendicular to the sidewall 41 and/or the base 43 of the cavity 40, and a proximal surface of the ridge(s) 47 can extend at an angle relative to the sidewall 41, base 43, and/or distal surface of the ridge(s) 47. A junction between the distal surface of a first ridge 47 and the proximal surface of a second ridge 47 that is adjacent and distal to the first ridge 47 can be rounded as shown, or may be more angular to form a relatively sharp corner. Other shapes and configurations for the ridges 47 are also possible. In some embodiments, the ridges 47 extend around the entire sidewall 41. In other embodiments, the ridges 47 can extend only partially around the sidewall 41.

FIGS. 9-12 illustrate the reverse insert 12 in greater detail. The reverse insert 12 is configured to couple with the stem face 36 by virtue of features shown in the exploded view of FIG. 7, assembled view of FIG. 1A, and assembled section view of FIG. 8. The reverse insert 12 includes a distal portion 50 and a proximal portion 52. The proximal portion 52 can include a concave proximal surface 54 configured to interface with a glenosphere or the like, which can be implanted in a patient's glenoid as part of a reverse prosthesis surgery. An outer wall 56 of the reverse insert 12 can be substantially cylindrical.

Figure 11:
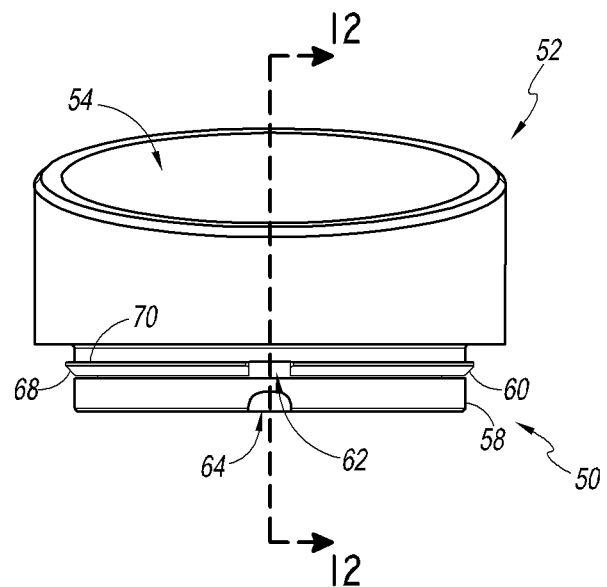
FIG. 11 is a first side view of the of the reverse insert of FIG. 9.
Figure 12:
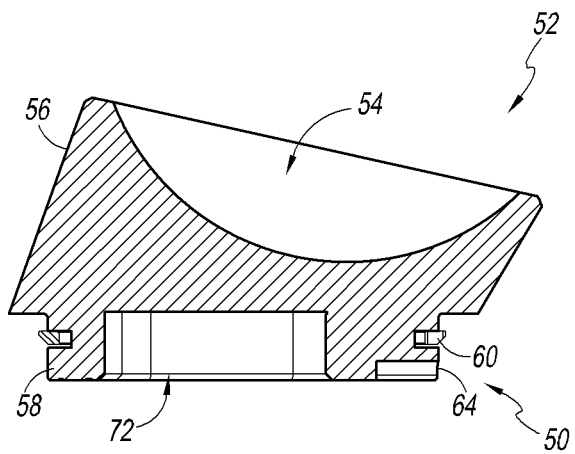
FIG. 12 is cross-sectional view of the reverse insert of FIGS. 9-11 taken through the section plane 12-12 in FIG. 11.

As shown in FIGS. 11 and 12, a top or proximal surface of the reverse insert 12 is angled relative to a bottom or distal surface. The angle between the bottom surface and the top surface is the inclination angle of the insert. The reverse insert 12 can be provided in a number of different inclination angles, for example 7.5°, 12.5°, and 17.5°. Other inclination angles are also possible. In some embodiments, the user can select among stems 30 having various angles between the normal axis A and the stem axis 31 as described herein and among reverse inserts 12 having various inclination angles to create a reverse shoulder prosthesis 10 having an overall angle selected and suited for the particular patient. For example, a reverse insert 12 having an inclination angle of 12.5° can be used with a stem 30 having an angle of 132.5° to create an overall angle of 145°.

The distal portion 50 of the reverse insert 12 includes a protrusion 58. The protrusion 58 can be integrally formed with the proximal portion 52 the reverse insert 12. In other words, the proximal portion 52 and protrusion 58 are monolithic or unitary. The protrusion 58 is configured to directly interface and couple with the cavity 40 of the stem face 36. For example, a peripheral surface of the protrusion 58 can form one part of a direct interface between the insert 12 and the stem face 36. Another part of the direct interface can include all or a portion of the sidewall 41 of the cavity 40. By providing the direct interface between the insert 12 and the stem 30, once the distal portion 32 of the stem 30 is lodged in the humerus, the insert 12 can be immediately applied to the stem 30 without the need for assembling a metaphysis or other intervening component. In some embodiments, the protrusion 58 couples with the cavity 40 via a snap-fit or friction fit. In the illustrated embodiment, the protrusion 58 is circular and configured to couple with the circular cavity 40 shown in FIGS. 3 and 6. Alternatively, in other embodiments, the protrusion 58 can be non-circular but rotationally symmetric to couple with a non-circular but rotationally symmetric sidewall 41. For example, the protrusion 58 can be shaped similarly to the locking protrusion of the reverse insert described in PCT Publication No. WO 2013/064569. As shown, the protrusion 58 can include an indexing marker 64 configured to assist with properly aligning the reverse insert 12 with the stem face 36.

Figure 7:
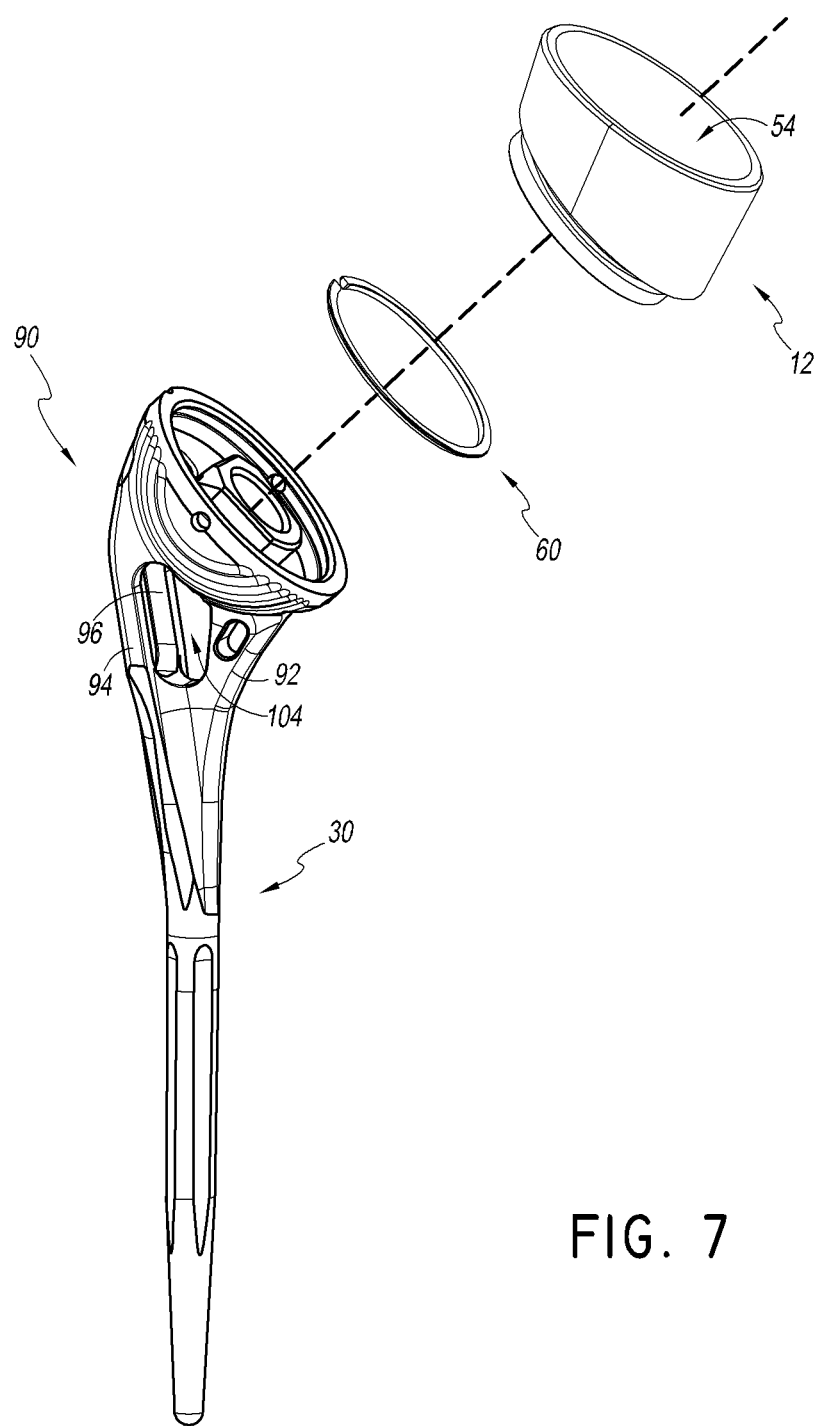
FIG. 7 is an exploded view of the reverse shoulder prosthesis of FIG. 1A.

The protrusion 58 can include one or more locking members. In the illustrated embodiment, the protrusion 58 includes a C-ring 60 for mechanically coupling the reverse insert 12 directly to the stem 30. As shown in FIG. 7, the C-ring 60 is formed separately from the reverse insert 12 and is snapped, pressed, or otherwise placed onto the protrusion 58 either permanently or removably. In other embodiments, the C-ring 60 or another locking member can be integrally formed with the protrusion 58. In the illustrated embodiment, the C-ring 60 includes a gap 62 that enables the C-ring to flex to facilitate insertion of the protrusion 58 into the cavity 40. The gap 62 can be aligned with the indexing marker 64. In some embodiments, the locking member is an O-ring or protrusion that extends around an entire outer periphery of the protrusion 58. In some embodiments, the locking member or members can be other deflectable members that can project away from the protrusion 58 less in one state to permit the protrusion 58 to be advanced into the cavity and can project away from the protrusion 58 more in another state to enable the locking member or members to project into engagement with the sidewall 41, e.g., into the groove 46. The C-ring 60 or other locking member is configured to engage or couple with the groove 46 of the stem face 36. The C-ring 60 can include a gradually ramped distal portion 68, and a perpendicular or right-angle stop portion 70 at a proximal end. The ramped portion 68 has a smaller diameter toward a distal portion thereof and a progressively lager diameter toward a proximal portion thereof. The ramped portion 68 allows the C-ring 60 to slide into the groove 46, and the stop portion 70 inhibits disengagement or removal of the C-ring 60 from the groove 46. In some embodiments, the C-ring 60 allows the reverse insert 12 to couple with the stem face 36 via a snap-fit.

Figure 8:
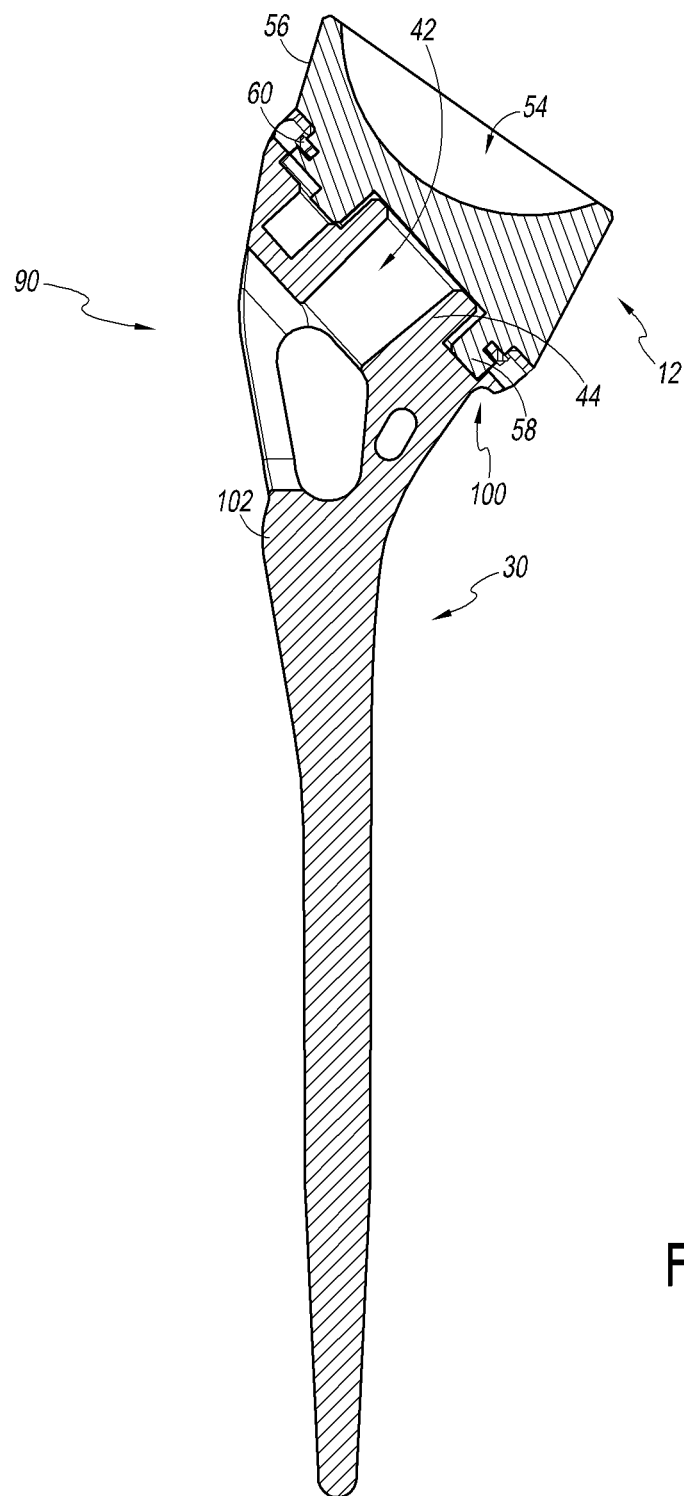
FIG. 8 is a cross-sectional view of the reverse shoulder prosthesis of FIG. 1A taken through section plane 8-8 shown in FIG. 1A.
Figure 8A:
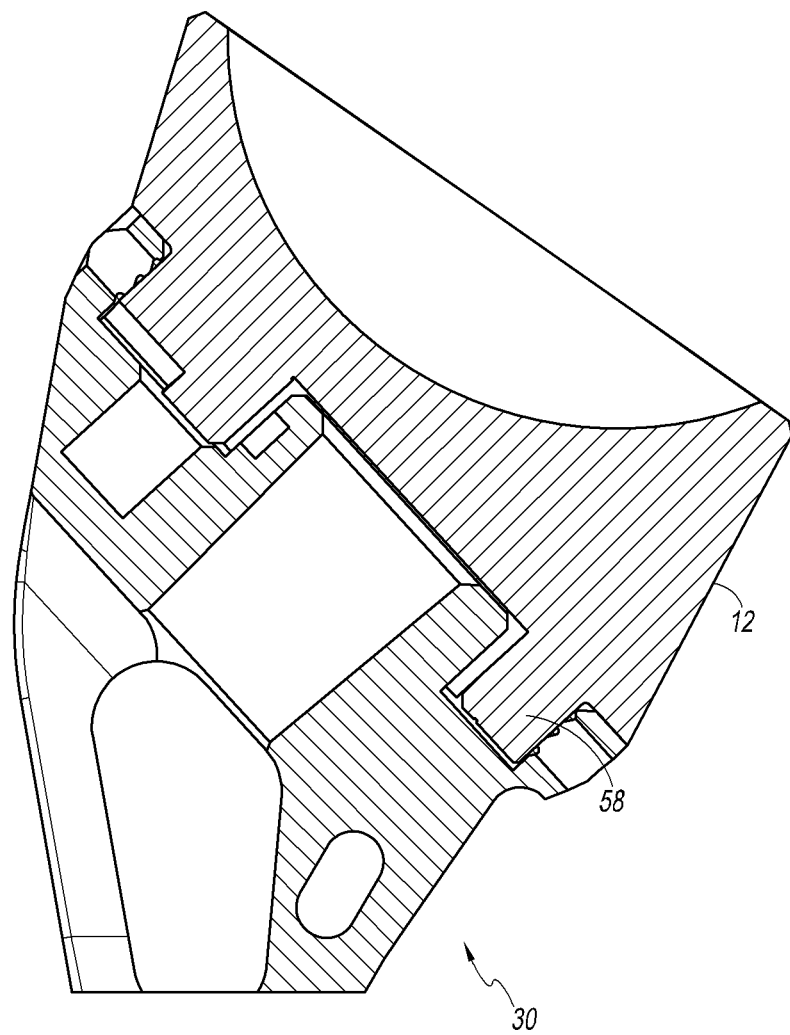
FIG. 8A is a detail cross-sectional view of another embodiment of a reverse shoulder prosthesis including the stem of FIG. 5A.
Figure 8B:
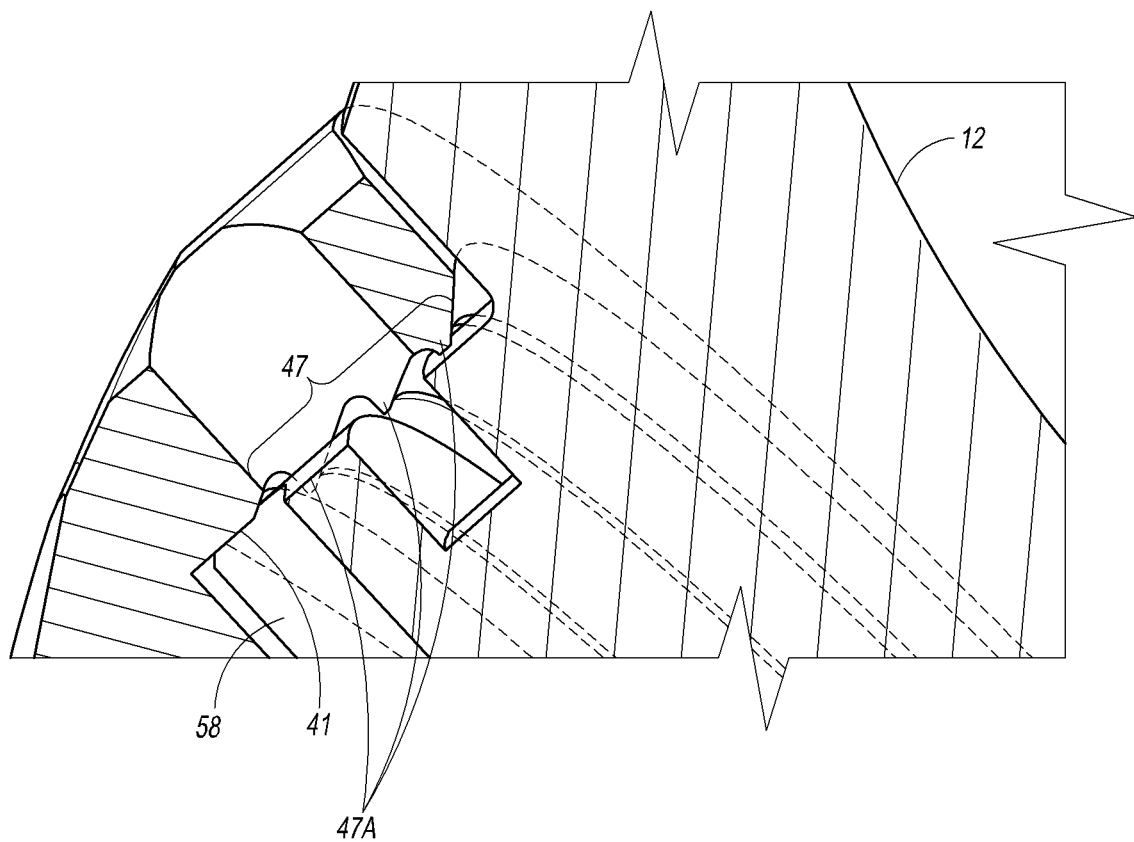
FIG. 8B is a detail view of a portion of the reverse shoulder prosthesis of FIG. 8A showing an interference fit between the stem and the reverse insert.
Figure 9:
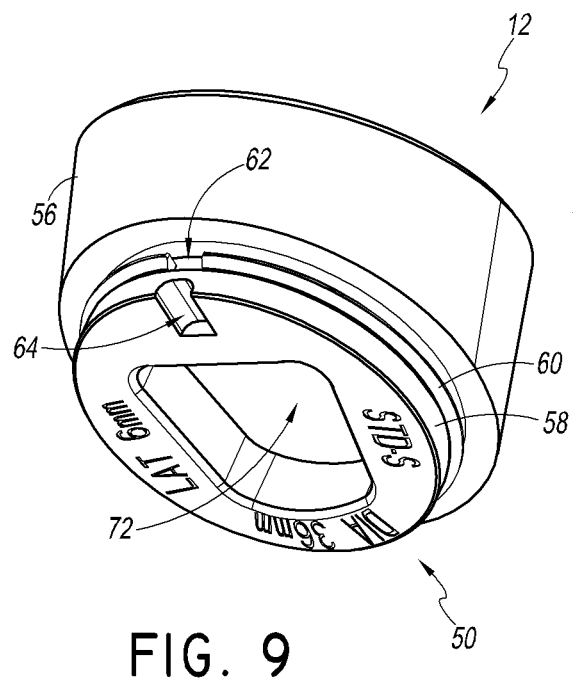
FIG. 9 is a bottom perspective view of the reverse insert of the reverse shoulder prosthesis of FIGS. 1A and 1B.

In the embodiment of the stem face 36' shown in FIG. 5A, the ridge(s) 47 can act as locking member(s) or feature(s). The inner periphery of the cavity 40 of the stem face 36' defined by the ridges 47 can be smaller than the outer periphery or an outer dimension of the protrusion 58. An interference fit can therefore be provided between the protrusion 58 and the cavity 40, e.g., the ridges 47, when the reverse insert 12 is engaged with or coupled to the stem 30 (as shown in FIGS. 8A-8B) or 30' or the humoral anchor 30" or 200. In particular, the outer periphery of the protrusion 58 of the reverse insert 12 is larger than a dimension of the cavity 40 defined transversely across the cavity 40 between peaks 47A of the ridges 47 on opposite sides of the cavity 40. The peaks 47A, where provided can be pointed or rounded in different embodiments. The outer periphery of the protrusion 58 of the reverse insert 12 is smaller than the dimension defined by the base of the ridge 47 or defined by the sidewall 41 from which the ridges 47 extend. As a result, the insert 12 can be inserted into the cavity 40 but with some interference with the peaks 47A of the ridges 47, providing an interference fit. In some embodiments, ridges could alternatively or additionally be provided on the protrusion 58 of the insert 12. In such an embodiment, the protrusion 58 may not include a C-ring 60 or other locking member, as shown in FIGS. 8A-8B. In some embodiments, the stem face 36, 36' and/or protrusion 58 can include other members or features that provide an interference fit between the protrusion 58 and the cavity 40 when the reverse insert 12 is engaged with or coupled to a humeral anchor.

Figure 10A:
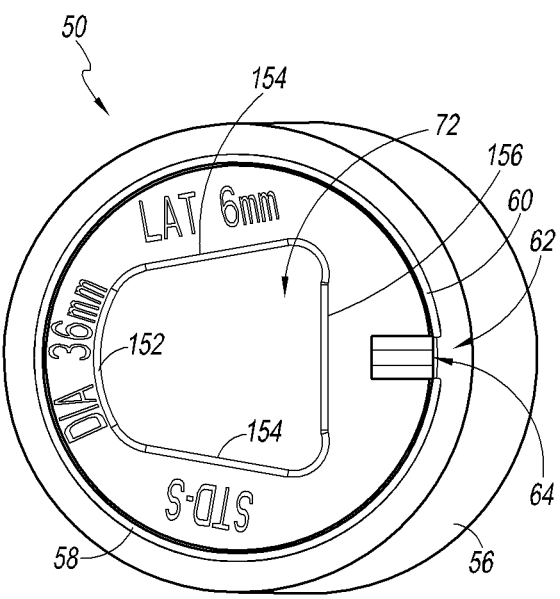
FIG. 10A is a bottom view of the reverse insert of FIG. 9.
Figure 10B:
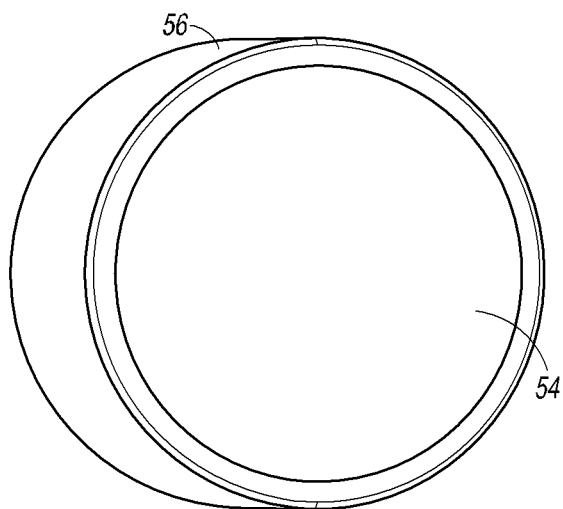
FIG. 10B is a top view of the reverse insert of FIG. 9.

A distal end of the protrusion 58 can include a recess 72. The recess 72 is configured to engage or receive the raised portion 44 of the stem face 36, for example, as shown in FIG. 8. In the illustrated embodiment, the recess 72 has a non-circular and radially asymmetric shape configured to correspond to the non-circular and radially asymmetric shape of the raised portion 44. As shown in FIG. 10A, the recess 72 can have a curved side 152 configured to correspond to the curved base 142 of the raised portion 44, angled edges 154 that angle outwardly from the curved side 152 and are configured to correspond to the angled sides 144 of the raised portion 44, and a straight side 156 configured to correspond to the straight top 146 of the raised portion. The shape of the recess 72 and raised portion 44 can help inhibit or resist rotation between the reverse insert 12 and the stem 30. For example, one or both of the recess 72 and the raised portion 44 can have at least one non-circular portion, e.g., a straight portion of a periphery to inhibit rotation of the insert 12 relative to the stem 30. The recess 72 and the raised portion 44 can have mating straight edge portions to inhibit such rotation. The recess 72 and the raised portion 44 can have multiple pairs of mating or matched straight edge portions to inhibit such rotation. The radially asymmetric shapes or rotation inhibiting configurations can help guide the surgeon in properly aligning or orienting the reverse insert 12 relative to the stem 30. Examples of alternative configurations for resisting rotation between the reverse insert 12 and the stem 30 are described in WO 2014/067961, the entirety of which is hereby incorporated by reference herein. Alternatively, in other embodiments, the recess 72 and raised portion 44 can have corresponding non-circular but rotationally symmetric shapes.

FIGS. 15-17B illustrate the anatomic insert 22 in greater detail. The anatomic insert 22 is configured to directly couple with the stem face 36 as shown in the assembled view of FIG. 2A and assembled section view of FIG. 14 by advancing the anatomic insert 22 along axis B shown in the exploded view of FIG. 13. The anatomic insert 22 includes a distal portion 80 and a proximal portion 82. The proximal portion 82 can include a convex proximal surface 84 configured to interface with the patient's glenoid. The distal portion 80 includes a protrusion 86. The protrusion 86 can be integrally formed with the proximal portion 82 such that the anatomic insert 22 is monolithic or a unitary body. The protrusion 86 is configured to interface and couple with the hole 42 of the stem face 36. In some embodiments, the protrusion 86 couples with the hole 42 via a snap-fit, press-fit, or friction fit. In some embodiments, the anatomic insert 22 is configured to rotationally engage the stem face 36. In the illustrated embodiment, the protrusion 86 and the hole 42 are circular and the protrusion 86 is configured to rotationally engage the hole 42. In some embodiments, the protrusion 86 can have a tapered profile and the hole 42 can have a corresponding tapered profile such that the protrusion is configured to correspond to the hole 42.

Figure 13:
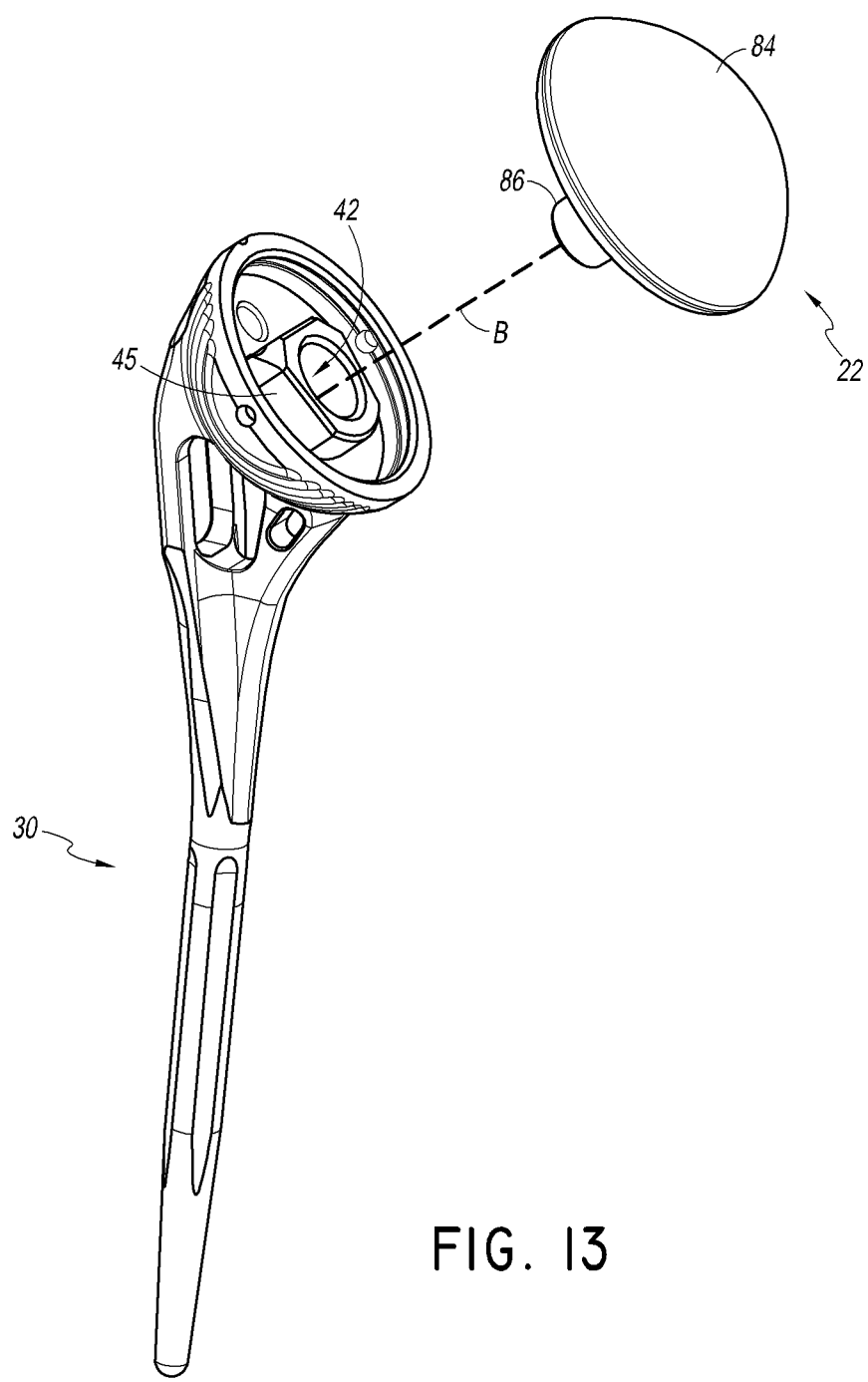
FIG. 13 is an exploded view of the anatomic shoulder prosthesis of FIGS. 2A and 2B.
Figure 14:
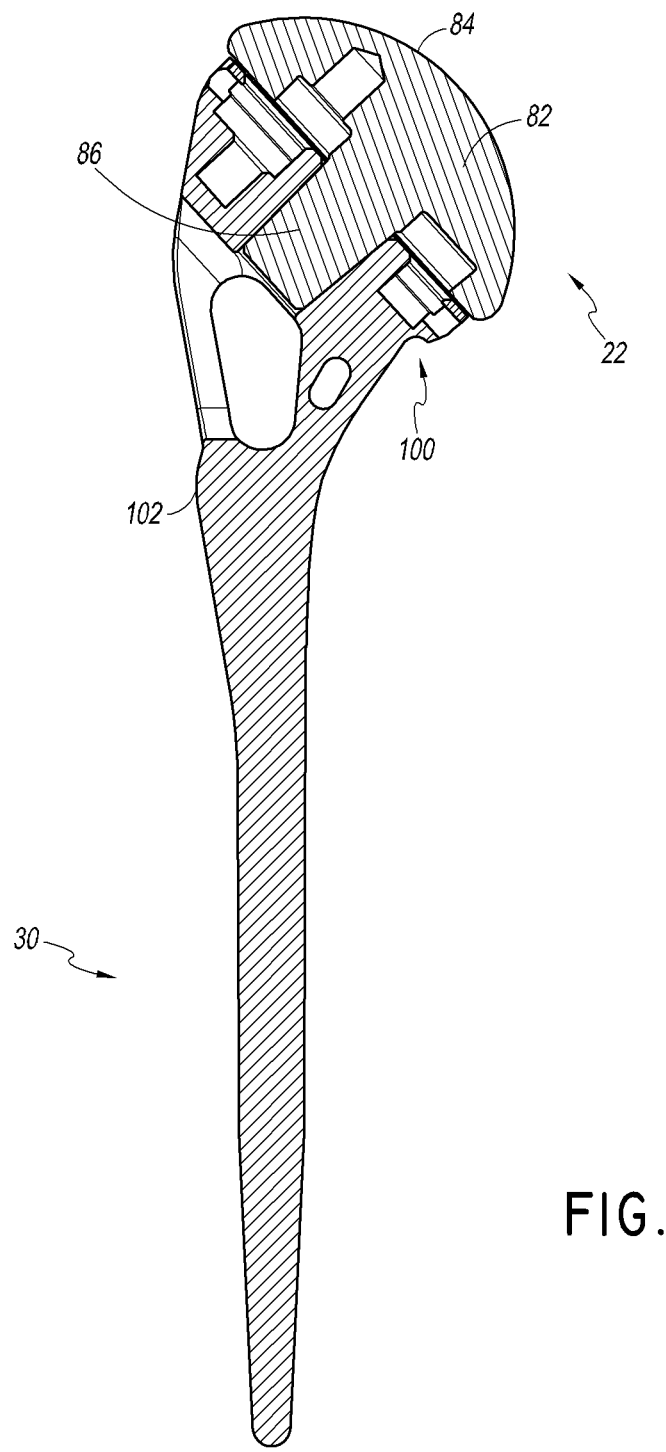
FIG. 14 is a cross-sectional view of the anatomic shoulder prosthesis of FIG. 2A taken through section plane 14-14 shown in FIG. 2A.
Figure 15:
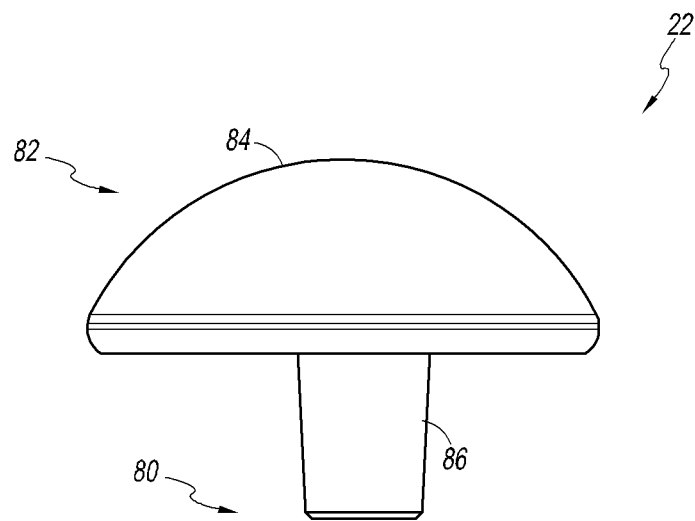
FIG. 15 is a side plan view of the anatomic insert of the anatomic shoulder prosthesis of FIGS. 2A and 2B.
Figure 16:
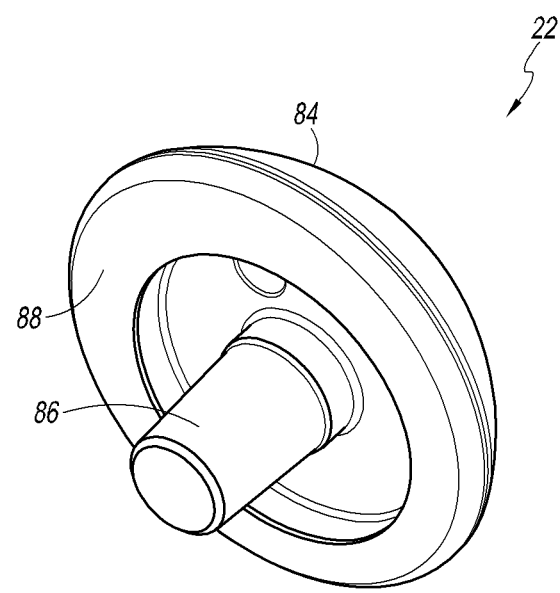
FIG. 16 is a bottom perspective view of the anatomic insert of FIG. 15.
Figure 17A:
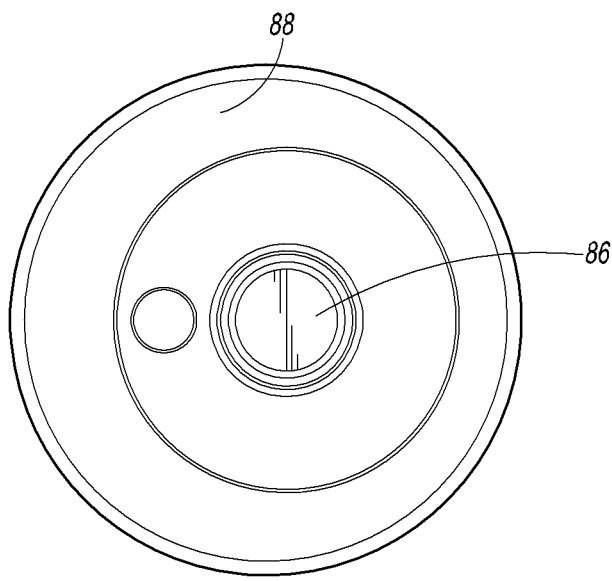
FIG. 17A is bottom view of the anatomic insert of FIG. 15.
Figure 17B:
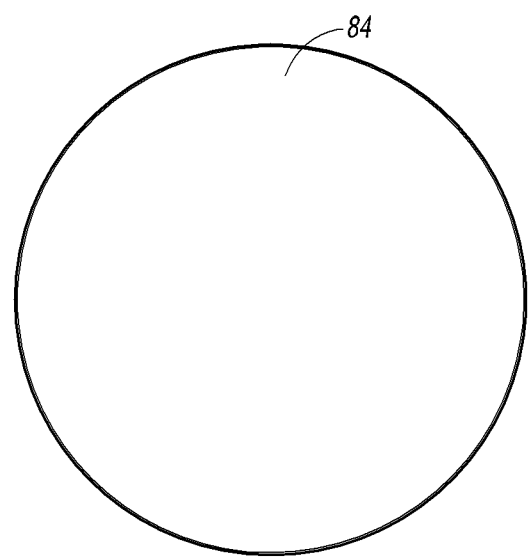
FIG. 17B is a top view of the anatomic insert of FIG. 15.

In some embodiments, for example as can be seen in FIGS. 6 and 15 and 17A, the center of the hole 42 is not aligned with a center of the cavity 40 or stem face 36, and a center of the protrusion 86 is not aligned with a center (e.g., a center of the convex proximal surface 84) of the anatomic insert 22. In other words, a central axis extending through the hole 42 (e.g., proximally and distally through the hole 42 or perpendicularly to the plane of the peripheral rim 38 of the stem face 36 as shown in FIG. 13) is offset from a central axis extending through the cavity 40 (e.g., proximally and distally through the cavity 40 or perpendicularly to the plane of the peripheral rim 38 of the stem face 36 as shown in FIG. 7). The convex proximal surface 84 of the anatomic insert 22 can be formed about a center of rotation, and a radius R of the anatomic insert 22 can extend through the center of rotation and the center of the convex proximal surface 84. An axis P extending through the center of the protrusion 86 can be offset from the radius R. This configuration advantageously allows for eccentric dialing of the anatomic insert 22. In other words, this configuration allows for eccentric rotation of the anatomic insert 22 about the axis P extending through the protrusion 86 when the anatomic insert 22 is coupled to the stem 30. Eccentric rotation moves the center of rotation of the articular surface of the anatomic insert 22 to a selected position relative to the axis extending through the protrusion. In some embodiments, the axis P of the protrusion 86 is offset from the radius R (or the center of rotation of the articular surface of the anatomic insert 22) by five to eight millimeters. In some embodiments, the anatomic insert 22 includes a distal rim 88 (shown in FIGS. 16 and 17A), and the protrusion 86 is offset from a center of the outer periphery of the rim 88 in a direction toward a relatively thinner region of the distal rim 88 (toward the right in FIG. 17A). In some embodiments, part or all of the distal rim 88 of the anatomic insert 22 (shown in FIGS. 16 and 17A) is configured to abut part or all of the peripheral rim 38 of the stem face 36 when the anatomic insert 22 is coupled to the stem face 36. This can advantageously provide tactile feedback to the user that the anatomic insert 22 is fully coupled with the stem face 36 and provide stability to the assembled anatomic prosthesis 20. However, in other embodiments, the distal rim 88 of the anatomic insert 22 does not abut the peripheral rim 38 of the stem face 36 in normal use to allow for adjustment of the anatomic insert 22 relative to the stem 30. For example, when a metallic or ceramic insert is used with a metallic stem 30, a gap is desired between the insert and peripheral rim 38 of the stem face. However, in alternate embodiments, when pyrolytic carbon is used as the insert or humeral head, contact between the metal stem and the pyrolytic carbon is preferred.

In some embodiments, the stem 30 is a fracture stem designed for use in procedures for proximal humeral fractures. An example of such a procedure is described in the Tornier Aequalis Fracture Shoulder Prosthesis Surgical Technique, which is hereby incorporated by reference herein. For example, the outer surface 35 of the proximal portion 34 could be selected based on a numerical simulation to provide accurate support to restore the tuberosities positions using virtual surgery. The stem 30 can further include a metaphyseal portion 90 between the shaft portion 32 and the proximal portion 34, as shown in FIGS. 3-8. The metaphyseal portion 90 includes three or more arms extending between and connecting the shaft portion 32 and the proximal portion 34. In the illustrated embodiment, the metaphyseal portion 90 includes three arms; a medial arm 92, a first lateral arm 94, and a second lateral arm 96. The medial arm 92 can be positioned near the calcar. The medial arm 92 is angled medially. In other words, a proximal end 110 of the medial arm 92 is positioned medially relative to a distal end 112 of the medial arm 92 as shown in FIG. 4B. The first 94 and second 96 lateral arms are configured and positioned to support the tuberosities. The first 94 and second 96 lateral arms are angled outwardly or laterally. In other words, a proximal end 114 of the first lateral arm 94 is positioned laterally relative to a distal end 116 of the first lateral arm 94, and a proximal end 118 of the second lateral arm 96 is positioned laterally relative to a distal end 120 of the second lateral arm 96 as shown in FIGS. 4B and 5. The angle and shape of each arms can be selected based on virtual surgery and/or a numerical simulation of bone strain due to the prosthesis to adapt to the particular patient bony anatomy. The use of the fracture stem 30 of the present disclosure in a fracture repair procedure advantageously helps promote tuberosity healing and inhibit or reduce tuberosity resorption.

The medial arm 92 can include one or more through holes 98. The through holes 98 can be configured to receive one or more sutures in a fracture repair procedure, for example as described in the Tornier Aequalis Fracture Surgical Technique and Tornier Aequalis Reversed Fracture Surgical Technique, each of which is hereby incorporated by reference herein. As shown in FIGS. 1-2 and 4B, the stem 30 can include a notch 100 at or near a location where a medial side 111 of the medial arm 92 meets the proximal portion 34. The notch 100 is configured to engage a suture in a fracture repair procedure and can help inhibit the suture from sliding or slipping out of position. The stem 30 can also include a fin 102 protruding from a lateral side of the shaft portion 32. In the illustrated embodiment, the fin 102 extends from a proximal portion of the shaft portion 32 distally along a portion of a length of the shaft portion 32. The fin 102 can help promote correct positioning of the stem 30 during stem placement.

Figure 23A:
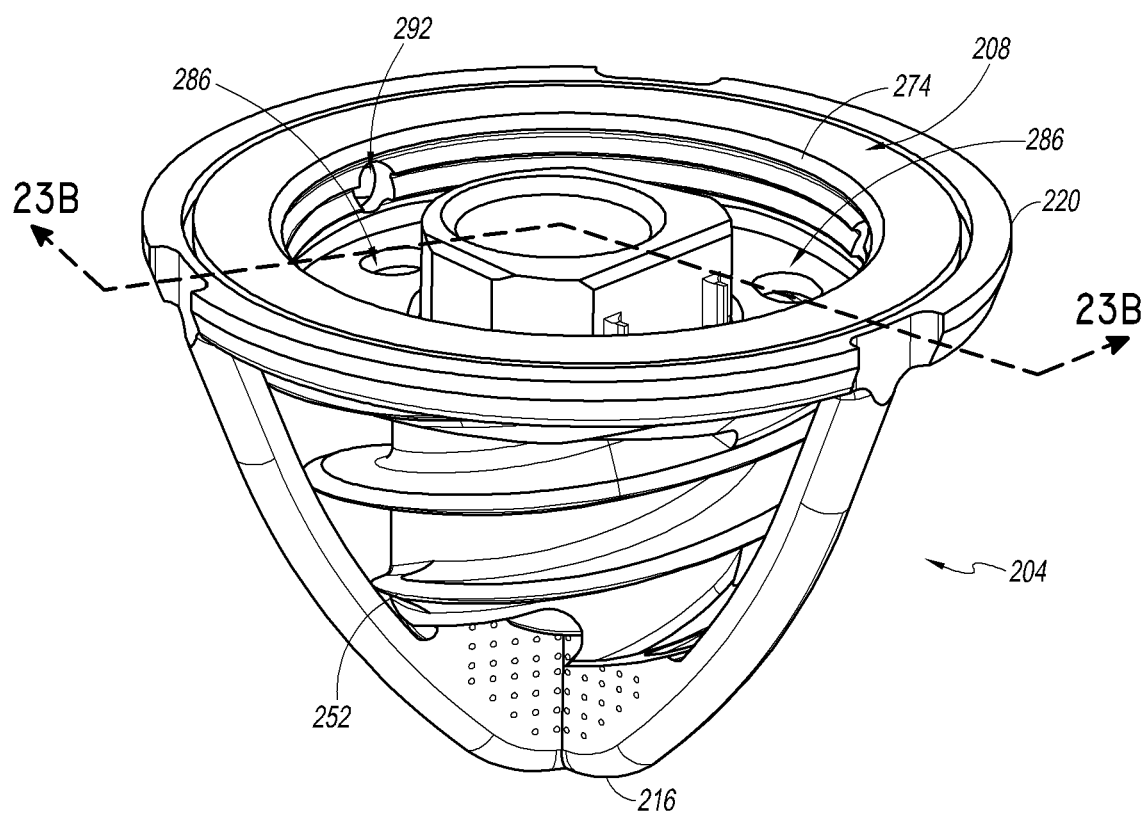
FIG. 23A is a top perspective view of a stemless humeral anchor.
Figure 23B:
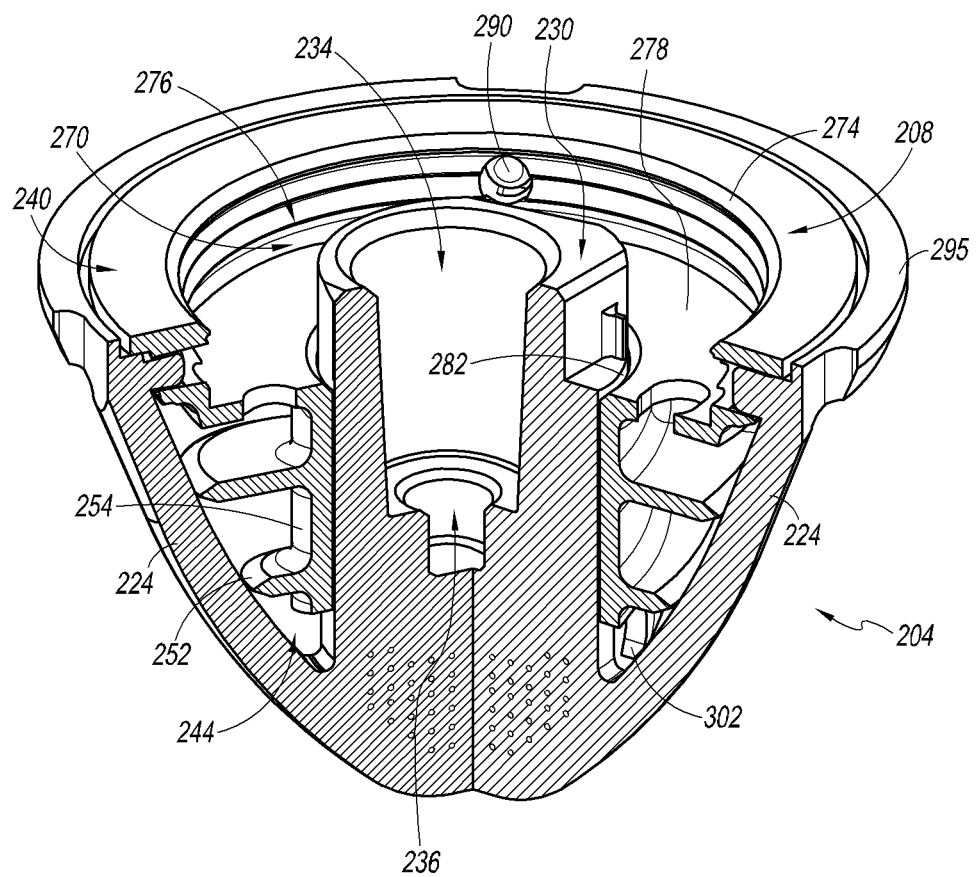
FIG. 23B is a cross-sectional view of the stemless humeral anchor of FIG. 23A, taken at the section plane 23B-23B.
Figure 23C:
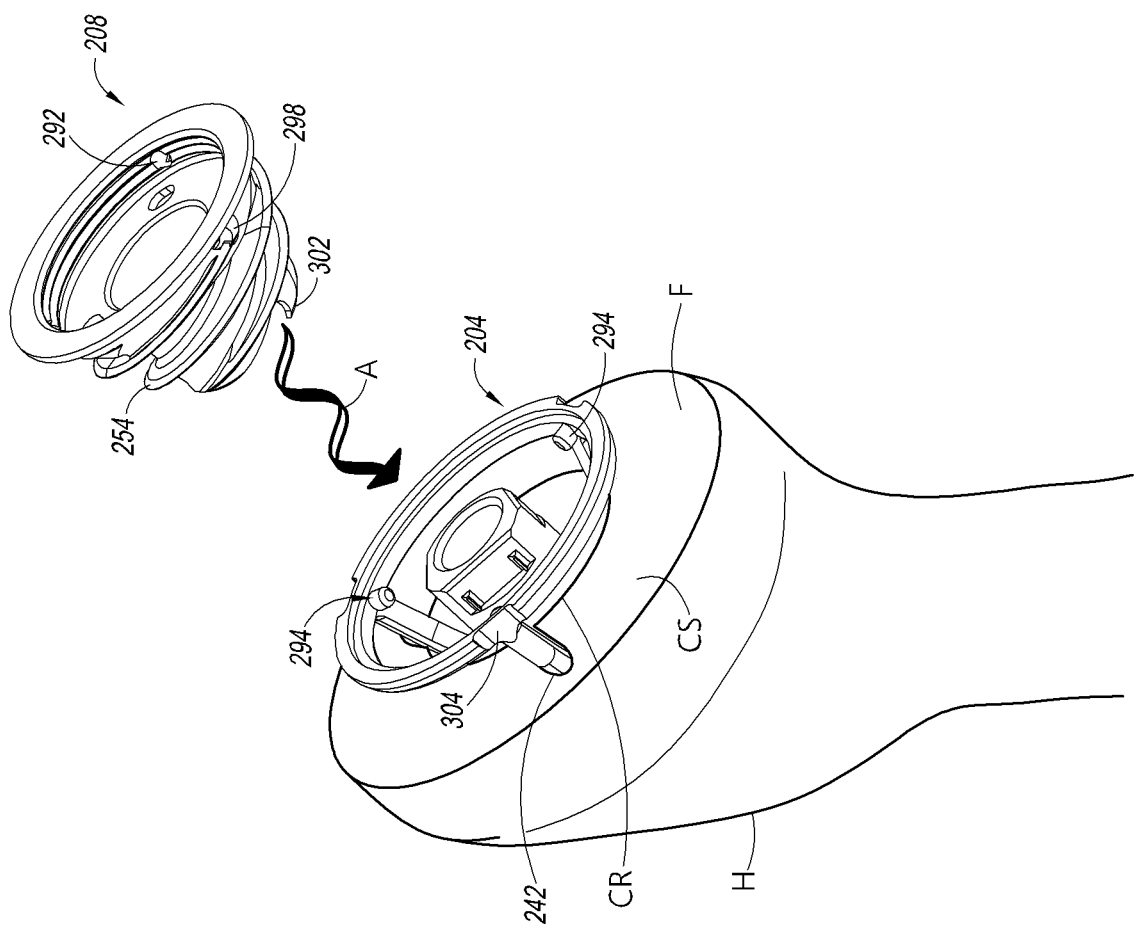
FIG. 23C is an exploded view of components of certain embodiments of the stemless humeral anchor of FIG. 23A shown in the context of the proximal humerus.

FIGS. 23A-23C illustrate an embodiment of a humeral anchor 200. The humeral anchor 200 is similar to the humeral anchor 30" except as described differently below. The features of the humeral anchor 200 can be incorporated into the humeral anchor 30" and the features of the humeral anchor 30" can be incorporated into the humeral anchor 200. In some embodiments, the humeral anchor 200 can include various features described in PCT Publication No. WO 2015/112307, the entirety of which is hereby incorporated by reference herein.

The humeral anchor 200 includes a base member 204 and an anchor component 208. The base member 204 has a distal end 216 configured to be embedded in bone. The base member 204 has a proximal end 220 configured to be disposed at a bone surface. The base member 204 having a plurality of spaced apart arms 224.

The humeral anchor 200 is configured to be secured to the humeral head 22 or any another anatomic insert described herein. For example, the humeral anchor 200 can comprise a concave member 230 comprising a hole 234 configured to receive the protrusion 86 or a distal shaft of an anatomical shoulder insert. In one embodiment, the concave member 230 comprises a body coupled with the arms 224 at or adjacent to the distal end 216 of the base member 204. A continuous expanse of material can be provided between the arms 224 and the body of the concave member 230. The body and the arms 224 can provided as a monolithic structure. The proximal end of the body of the concave member 230 can comprise an opening into which the hole 234 extends. The proximal end of the concave member 230 can include other features of the raised portion 44 of the stem 30. Other features of the proximal portion of the stem 30 that can be incorporated in to the proximal end of the concave member 230 include that the proximal end of the concave member 230 can be in the same plane or substantially the same plane as the proximal end 240 of the anchor component 208, just as the raised portion 44 can be in the same plane as the peripheral rim 38 of the stem face. Also, the concave member 230 can be non-circular and radially asymmetric, e.g., having a flat peripheral edge to resist rotation or circular or non-circular but rotationally symmetric if rotation of the reverse insert is desired. Also, the sidewall of the cavity could be non-circular but rotationally symmetric in some embodiments. The disclosure of these and other features, including flats surfaces to resist rotation, should be considered as incorporated herein. The concave member 230 is enclosed at a distal end of the hole 234. The enclosed distal end of the hole 234 can include a tool interface 236, as shown in FIG. 23B. The tool interface can aid in coupling a tool for placement of the base member 204 with the proximal humerus.

The anchor component 208 has a proximal end 240 and a distal portion 244 advanceable into the base member 204 to a position disposed within the arms 224. In the embodiments depicted in FIGS. 23-23C, the distal portion 244 of the anchor component 208 comprises threads 252. The distal portion 244 can also include a cylindrical sleeve 254. The threads 252 can project laterally from the cylindrical sleeve 254. The inner periphery of the sleeve 254 can be selected to allow the anchor component 208 to be advanced over the body of the concave member 230. For example, the sleeve 254 can have a circular inner periphery that has a diameter larger than the outer circular periphery of the body forming the concave member 230. The relative sizes of the outer periphery of the body forming the concave member 230 and the sleeve 254 can be selected such that there is no resistance to advancement of the sleeve 254 relative to the body but such that a close fit is provided, e.g., a slip fit.

The threads 252 project circumferentially into a space between the arms 224 when the anchor component 208 is disposed within the base member 204. The threads 252 are exposed between the arms 224 when the anchor component 208 is advanced into the base member 204. As such the threads 252 are able to project into the cancellous bone in the proximal humerus to create secure connection between the humeral anchor 200 and the bone tissue. This structure creates a secure connection even before any ingrowth of bone matter into the anchor, e.g., initially at implantation of the humeral anchor 200. This improved initial pullout force greatly reduces the chance of dislodgement, as discussed below in connection with FIG. 23D.

The proximal end 240 of the anchor component 208 partly defines the proximal face of the humeral anchor 200. The proximal end 240 includes features for securing the reverse insert 12 or another reverse shoulder humeral component at the proximal face. For example, a cavity 270 can be provide in the humeral anchor 200 that is at least partially defined by the anchor components 208. In one embodiment, the cavity 270 located at the proximal face of the humeral anchor 200 has an outer periphery defined by an outer peripheral sidewall 274. The cavity 270 has a distal wall 278 extending radially inwardly from a distal portion of the sidewall 274. The distal wall 278 can extend from the sidewall 274 to an aperture 282 of the anchor component 208. The aperture 282 is configured to be advanced over the proximal end of the concave member 230.

The outer peripheral sidewall 274 can include any suitable feature for securing an insert, e.g., a reverse insert, therein. As discussed above, a C-ring, an interference fit, a fastener or other securement device can be provided for securing an insert. FIG. 23B shows that one or a plurality of ridges 276 can be provided on the outer peripheral sidewall 274. The ridges 276 are sized to define an inner periphery that is equal to or preferably smaller than the outer periphery of the distal projection of the insert 12. The size difference is that sufficient to create an interference fit in some embodiments. Preferably the ridges 276 extend entirely around the outer peripheral sidewall 274. The ridges 276 could extend along arcs including less than 180 degrees of the inner periphery. The ridges 276 could extend along arcs including less than 90 degrees of the inner periphery. The ridges 276 could extend along arcs including less than 45 degrees of the inner periphery. The ridges 276 could extend along arcs including less than 30 degrees of the inner periphery. The ridges 276 could extend along arcs including greater than 180 degrees of the inner periphery.

FIG. 23A shows that the proximal face of humeral anchor 200, which is defined in part by the anchor component 208, includes a driver interface 286 disposed thereon. The driver interface 286 can be formed on the distal wall 278 in an expanse thereof disposed between the aperture 282 and the sidewall 274. The driver interface 286 provides a convenient connection point for a tool to secure to the anchor component to enable the anchor component to be advanced by action of the threads 252 into the bone. The driver interface 286 can include two apertures that are formed through the distal wall 278. The apertures can be simultaneously engaged by a tool and can each bear about one-half of the torque applied to the anchor component 208 to advance it into the base member 204.

Although the threads 252 can be self-tapping in that they cut their own path into bone, in some cases a guide structure 290 is provided on the base member 204. The guide structure 290 can include a plurality of, e.g., two, three or more than three posts 294 that project from the base member 204 into the threads 252 and ride along the threads as the anchor component 208 is being advanced into the base member 204. In one embodiment, the guide structure includes a post 294 disposed on a side of each of the arms 224 and projecting inwardly into a space within the arms 224. In one embodiment, the anchor component 208 has an arcuate, e.g., a semicircular, wall 298 disposed at the ends of the threads 252. The wall 298 is configured to receive the posts 294 when the anchor component 208 is fully advanced. That is the posts come to rest against or adjacent to the wall 298. Further the posts 294 can be viewed through apertures 292 formed in the sidewall 274 of the anchor member 208. When the posts 294 are disposed against the wall 298 and visible through the apertures 292, the anchor component 208 is shown to be fully advanced within the base member 204.

The rim 295 provides a sufficiently rigid connection between the arms 224 to prevent or reduce deflection of the arms 224 during torqueing of the anchor member 208. The rim 295 positions the posts 296 to be in the proper position to be received in the apertures 292.

FIG. 23C shows the humeral anchor being disposed in the proximal humerus h. The proximal humerus H is resected to create an exposed face F. The face can be prepared by creating a countersunk region CS and by forming a created recess CR. The created recess CR can include radial projections that mirror the shape of the arms 224 such that the base member 204 can be urged into the cancellous bone of the proximal humerus H under relatively low force. In the illustrated embodiment, the base member 204 has a tool interface 304, for example a concave recess formed along the outer periphery of the rim 295. FIG. 23C shows that the rim 295 can have three such concave recesses, for example one corresponding to the position of each of the arms 242. Once so placed, the anchor component 208 can be rotated into the base member 204 as indicated by arrow A and as discussed above. In particular, the posts 294 can be aligned with the threads 254. The anchor component 208 can be rotated with the posts 294 sliding in the threads 254. Leading faces of the threads can have cutting edges 302 to clear a path for the anchor component 208 with reduced to minimal force. The anchor component 208 can be advanced until the posts 294 come to rest against the wall 298 and/or are visible through the apertures 292.

Figure 23D:
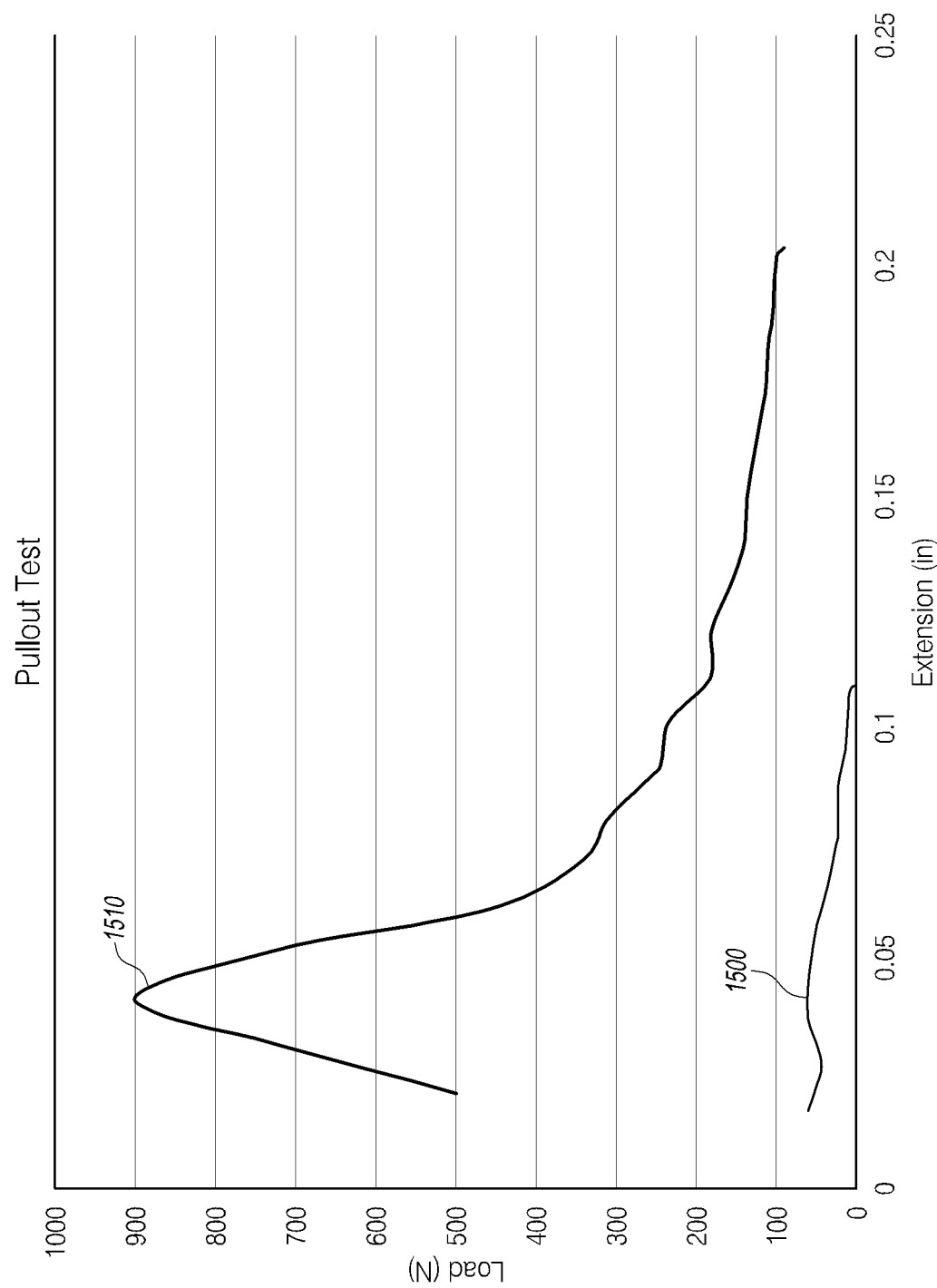
FIG. 23D illustrates the performance of various embodiments of stemless humeral shoulder assemblies similar to those illustrated in FIGS. 23-23C.

FIG. 23D illustrates the performance of certain embodiments of humeral anchors similar to the humeral anchor 200 compared to a prior art design. In particular, FIG. 23D illustrates the initial pull-out force 1510 for Embodiment A, a variant of the humeral anchor 200 in which the anchor member 208 has a single continuous thread. Portions of a helical structure of the anchor member 208 project into the open area defined between the arms 224 and engage the bone thereby increasing the initial pull-out force of the humeral anchor 200 when initially placed. As shown in FIG. 23D, the peak force corresponding to the initial pull out force 1510 of Embodiment A is at least ten times greater than the peak force corresponding to the initial pull out force 1500 of the prior art design having a base member and no anchor thread.

Figure 24:
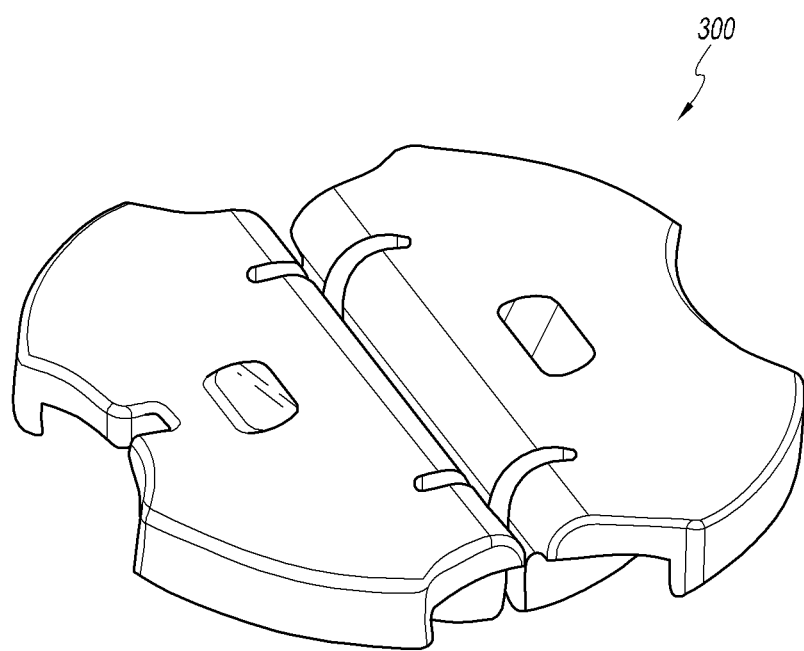
FIG. 24 illustrates a perspective view of a stem holder.
Figure 25A:
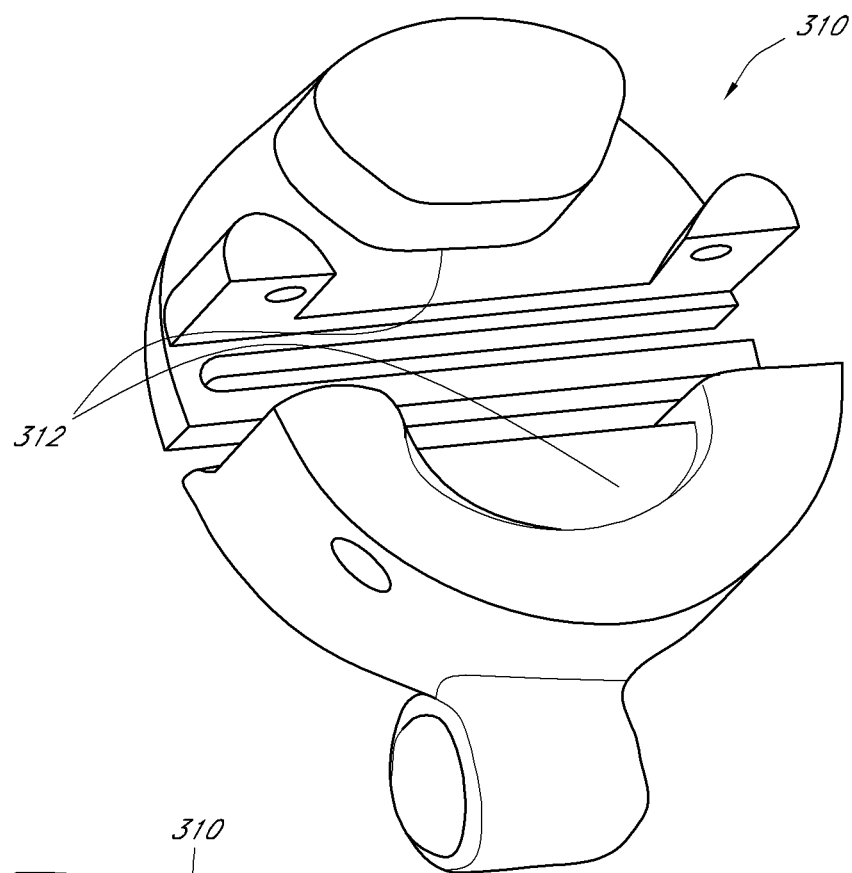
FIG. 25A illustrates a perspective view of a different embodiment of a stem holder.
Figure 25B:
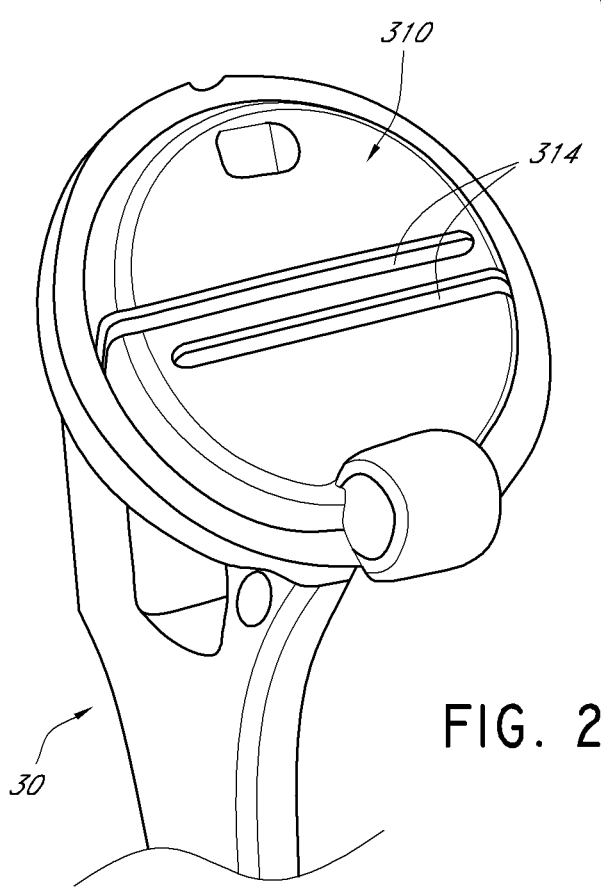
FIG. 25B illustrates a perspective view of the stem holder of FIG. 25A engaging a stem of the present disclosure.

A stem holder or inserter can be used to hold the stem and/or impact it into bone during stem placement. FIG. 24 illustrates an example embodiment of a stem holder 300 configured to be used with an inserter. The plate includes two jaws and two springs to ensure retention with the stem and inserter. FIG. 25A illustrates another example embodiment of a stem holder 310 configured to be used with stems having a proximal face 36 as described herein, and FIG. 25B illustrates the stem holder 310 of FIG. 25A coupled to the stem 30. The stem holder 310 can be monolithic or manufactured in one piece. The stem holder 310 can be made of an elastic alloy, for example, titanium or a cobalt-chromium alloy. In the illustrated embodiment, the stem holder 310 is deformable or spring like, which allows the stem holder 310 to be self-retaining on the proximal face 36 of the stems shown and described herein. The stem holder 310 couples to the stem face 36 via a snap fit. A distal side of the stem holder includes compression features 312 as shown in FIG. 25A. The raised portion 44 of the stem face 36 is received between the compression features 312 as shown in FIG. 25B. As also shown in FIG. 25B, a proximal side of the stem holder includes deformable features 314 (e.g., slots extending across the stem holder 310) that allow the stem holder to flex to be coupled to and removed from the stem face 36. An inserter, for example as shown and described at least in FIGS. 24A-24D and corresponding description of WO 2014/067961, can be coupled to the stem holder 310 to insert the stem 30 into the humerus.

Figure 3:
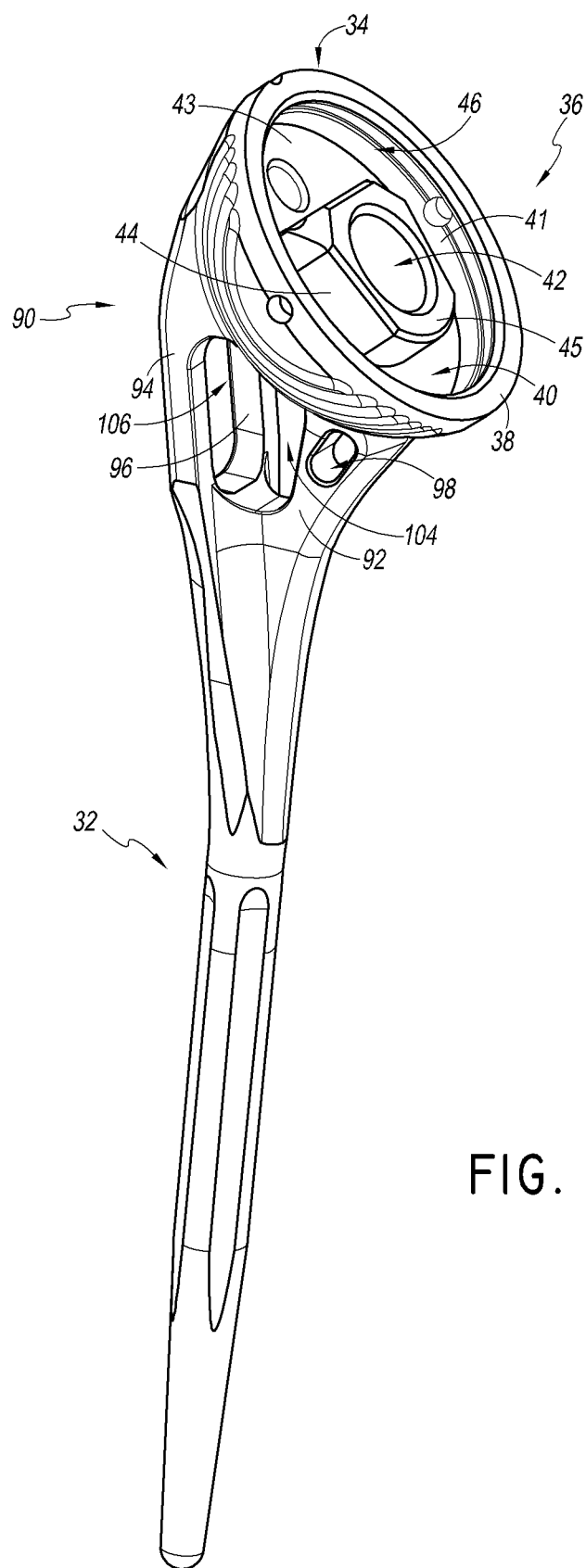
FIG. 3 is a perspective view of a humeral stem that is used in the shoulder prostheses of FIGS. 1A and 2A.
Figure 4C:
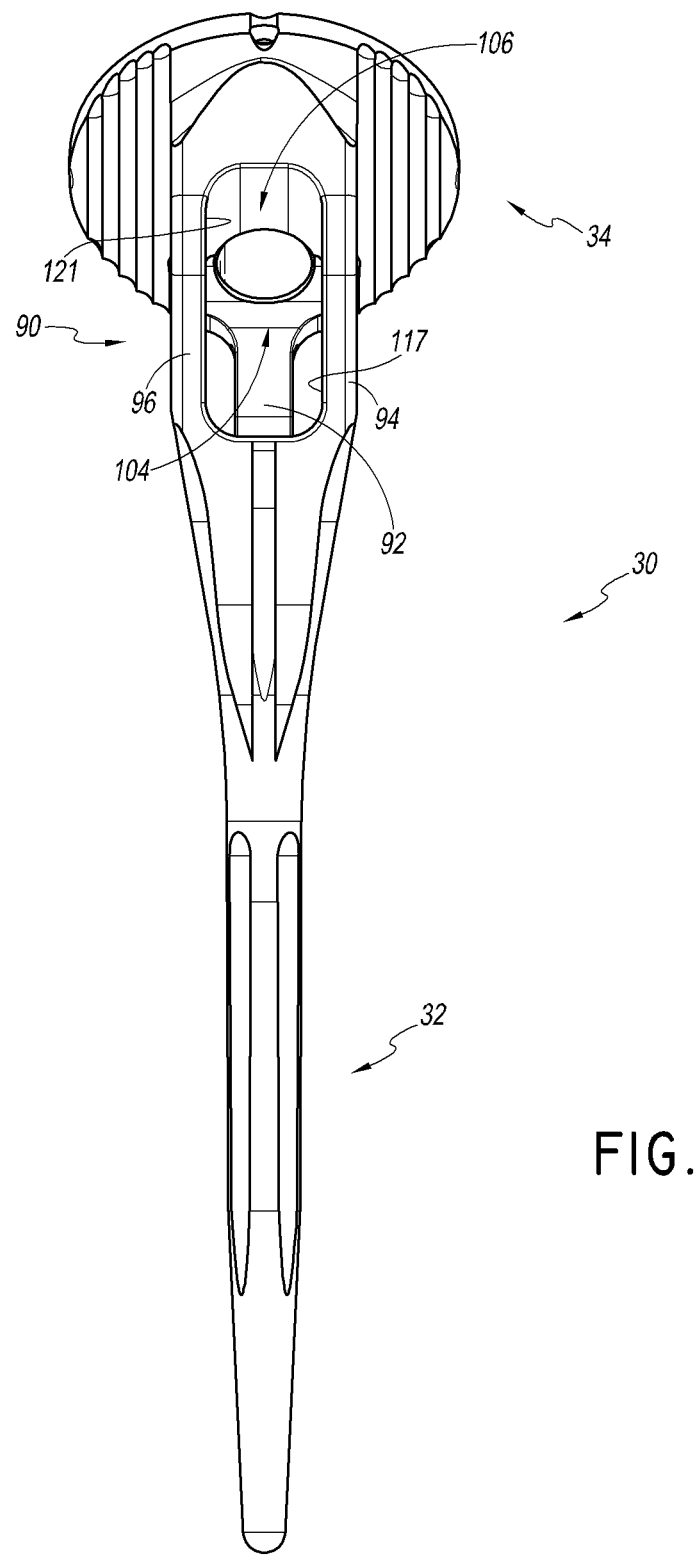
FIG. 4C is a third, alternate view of the stem of FIG. 3.
Figure 4D:
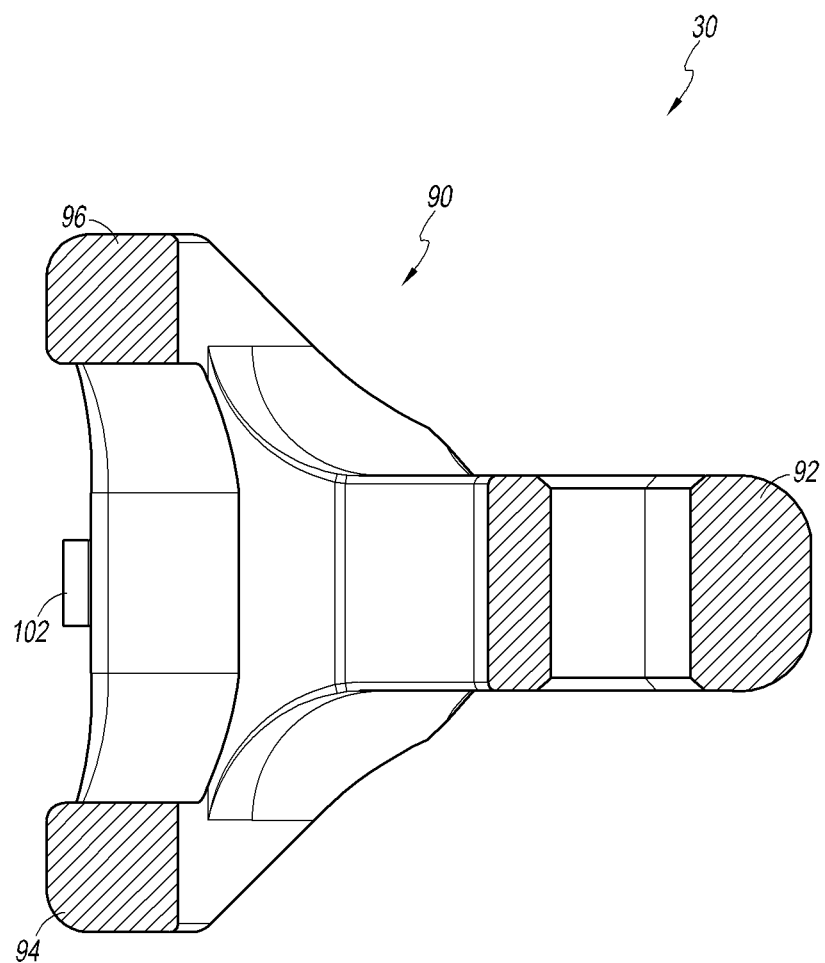
FIG. 4D is a cross-sectional view of the stem of FIG. 3 taken through the section plane 4D-4D in FIG. 4B.

A fenestration or window 104 is defined between a lateral edge 113 of the medial arm 92 and medial edges 115, 119 of the first 94 and second 96 lateral arms, respectively. In the illustrated embodiment, the hole 42 extends and is open to the window 104 as shown in FIG. 5. In some embodiments of a fracture repair procedure, a bone graft can be placed in the fenestration 104 to help promote bone-to-stem 30 fixation. A space or gap 106, shown in FIGS. 3 and 4C, is defined or formed between an inner edge 117 of the first lateral arm 94 and an inner edge 121 of the second lateral arm 96. In the illustrated embodiment, the gap 106 has an elongated, rounded rectangular shape, although other shapes or configurations are also possible. As shown, the gap 106 can extend from the proximal portion of the shaft portion 32 to the proximal portion 34. The space 106 may enable increased bone growth and fixation, for example enabling bone graft materials to be placed within the fenestration 104, within the space 106, and/or on a lateral side of the lateral arms 94, 96. For example, in some procedures, the stem 30 can be used in a tuberosity fixation procedure using a horseshoe graft. An example of such a procedure is described in Levy, Jonathan C. and Badman, Brian, Reverse Shoulder Prosthesis for Acute Four-Part Fracture: Tuberosity Fixation Using a Horseshoe Graft, J Orthop Trauma, Volume 25, Number 5, May 2011, which is hereby incorporated by reference herein. In such a procedure, the horseshoe graft can be placed on the lateral surface of the metaphyseal portion 90. The design of the metaphyseal portion 90 helps provide stability to the horseshoe graft. The space 106 allows the horseshoe graft to form or grow into or through the window 106 and improve fixation and tuberosity repair. In particular, resorption of the tuberosities can be reduced or prevented because more pathways for formation or growth of bone are provided to bridge between the fractured portions. The peripheral rim 38 of the stem face 36 can also help support and stabilize the tuberosities. The shape and size of the horseshoe graft can be selected based on a numerical simulation to accurately restore the tuberosities positions using virtual surgery.

Figure 26A:
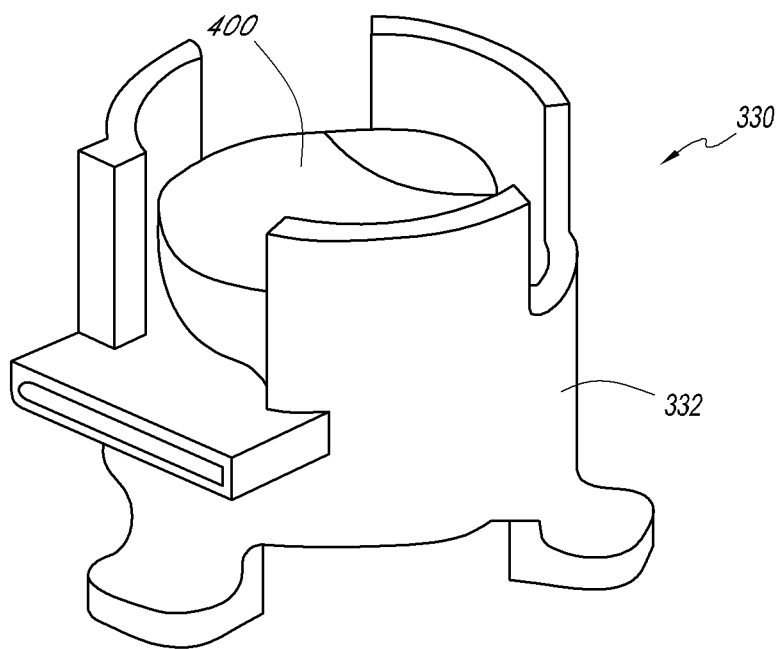
FIGS. 26A-E illustrate a perspective views of a bone cutter of the present disclosure.
Figure 26B:
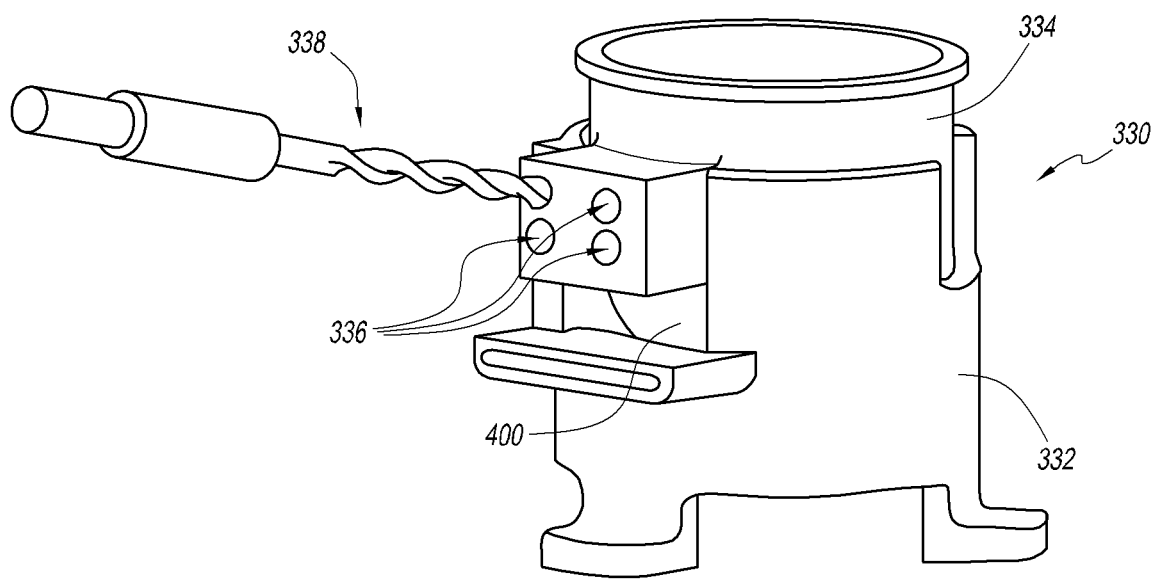
Figure 26C:
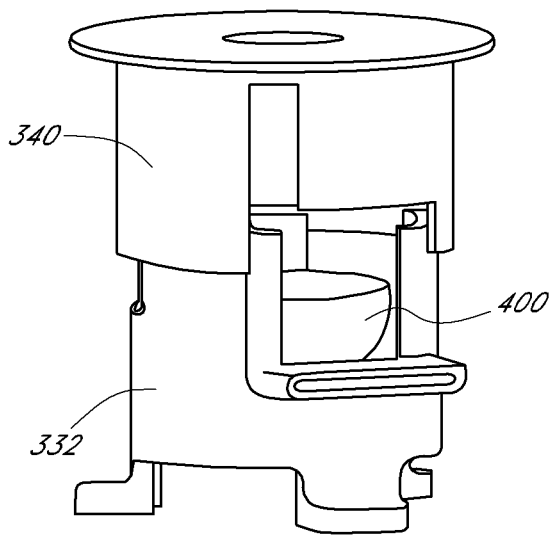
Figure 26D:
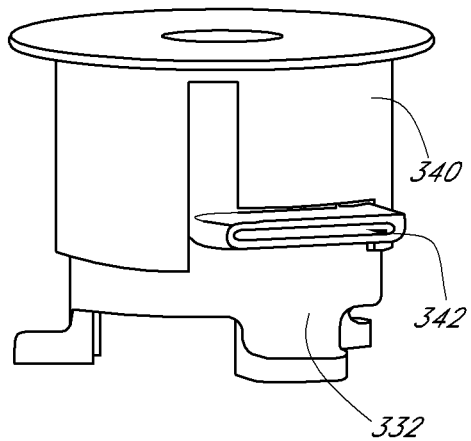
Figure 26E:
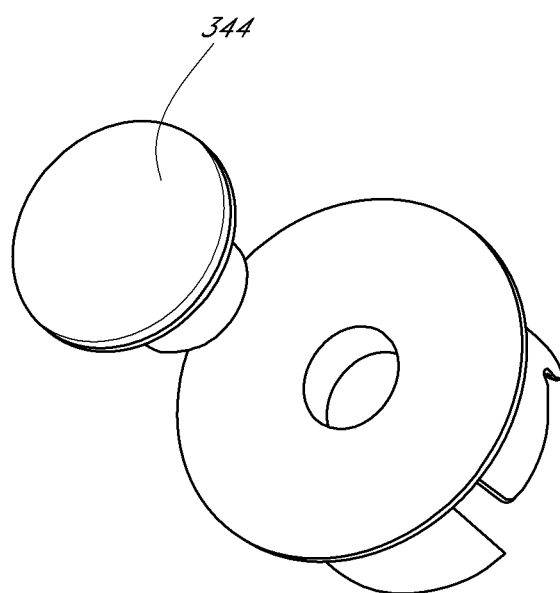
Figure 27C:
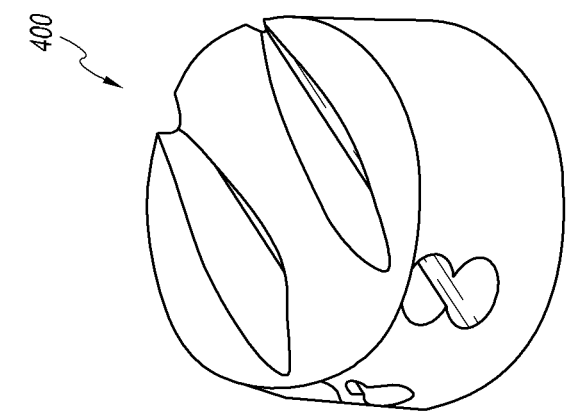
FIGS. 27A-C illustrate a perspective views of a bone graft of the present disclosure.
Figure 27B:
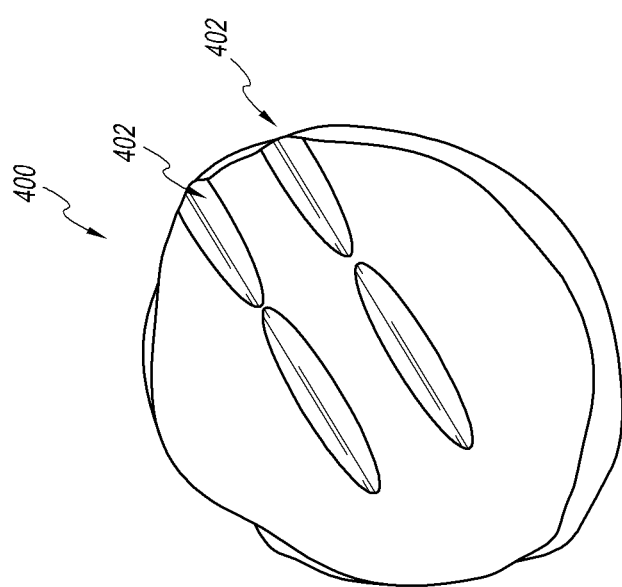
Figure 27A:
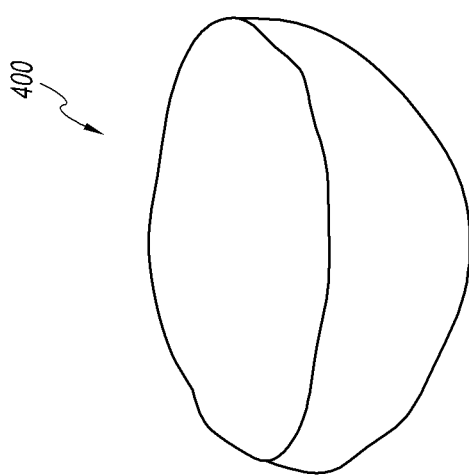
Figure 28A:
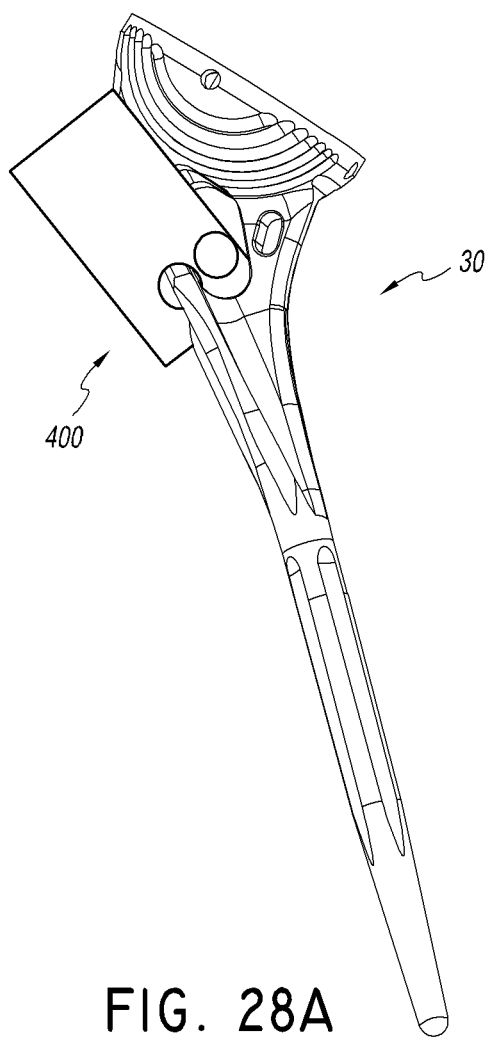
FIGS. 28A-B illustrate a perspective view of a fracture stem receiving the bone graft of FIG. 27C.
Figure 28B:
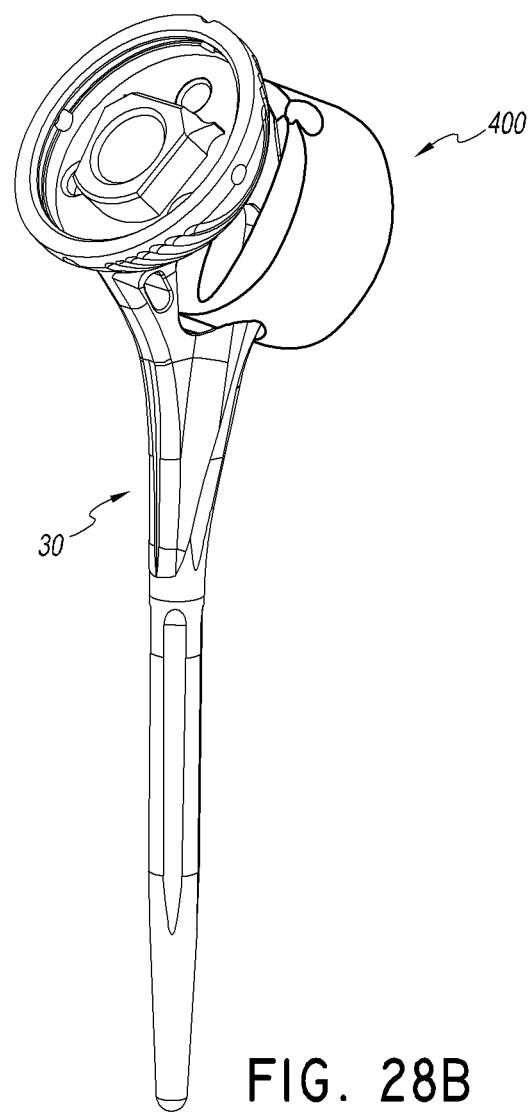

FIGS. 26A-E illustrate a bone cutter 330 that can be used to prepare the bone graft according to embodiments of the present disclosure. To prepare the bone graft, the resected humeral head or other bone graft material 400 is placed in a base 332 of the bone cutter 330 (with the cut side facing upwards or the top when using the humeral head), as shown in FIG. 26A. A drilling guide 334 including holes 336 is placed onto the bone graft 400, and a drill bit 338 is used to drill holes into the bone graft 400 through the holes 336 as shown in FIG. 26B. In the illustrated embodiment, the drilling guide 334 includes four holes 336 so that the drill bit 338 can be used to drill four holes into the bone graft 400. The holes 336 can be provided at different angles to create two angled grooves in the bone graft 400 that allow the prepared bone graft to fit the metaphyseal portion 90 of the fracture stem 30. Each grooves fit over the lateral arms 94 and 96 so that the inner portion of the graft fill the gap 106 and the window 104. A cutting cap 340 is placed on top of the base 332 applying pressure to secure the bone graft 400 inside the bone cutter 300 as shown in FIG. 26C. The cutting cap 340 is impacted on top with a mallet until the cutting cap 340 contacts the base 332 as shown in FIG. 26D to shape a diameter of the bone graft 400 into a cylinder. A saw blade is placed through a slot 342 to further shape the bone graft into a cylinder (for example, by cutting off the rounded bottom portion of the humeral head). The bone graft is extracted by pushing with an instrument 344 as shown in FIG. 26E. FIG. 27A illustrates the humeral head or other bone graft material 400 prior to be prepared using the bone cutter 330, FIG. 27B illustrates the bone graft material 400 including angled grooves 402 after the holes are drilled using the drilling guide 334, and FIG. 27C illustrates the prepared bone graft 400. The bone graft material 400 may be snap or press-fit onto the fracture stem. FIGS. 28A-28B illustrate the prepared bone graft 400 disposed on the fracture stem 30. A kit for a shoulder prosthesis can include a fracture stem as shown and described herein, the bone cutter 300, a drill, a mallet, and/or bone graft material. The bone graft material can be, for example, autograft or allograft, and can be made of bone, stem cells, a ceramic, or a polymer. Additional details regarding devices and methods involving placement of bone graft during a shoulder prosthesis procedure can be found in U.S. 2008/0183297, the entirety of which is hereby incorporated by reference herein.

Figure 18:
FIG. 18 is a side view of a humerus.
Figure 19:
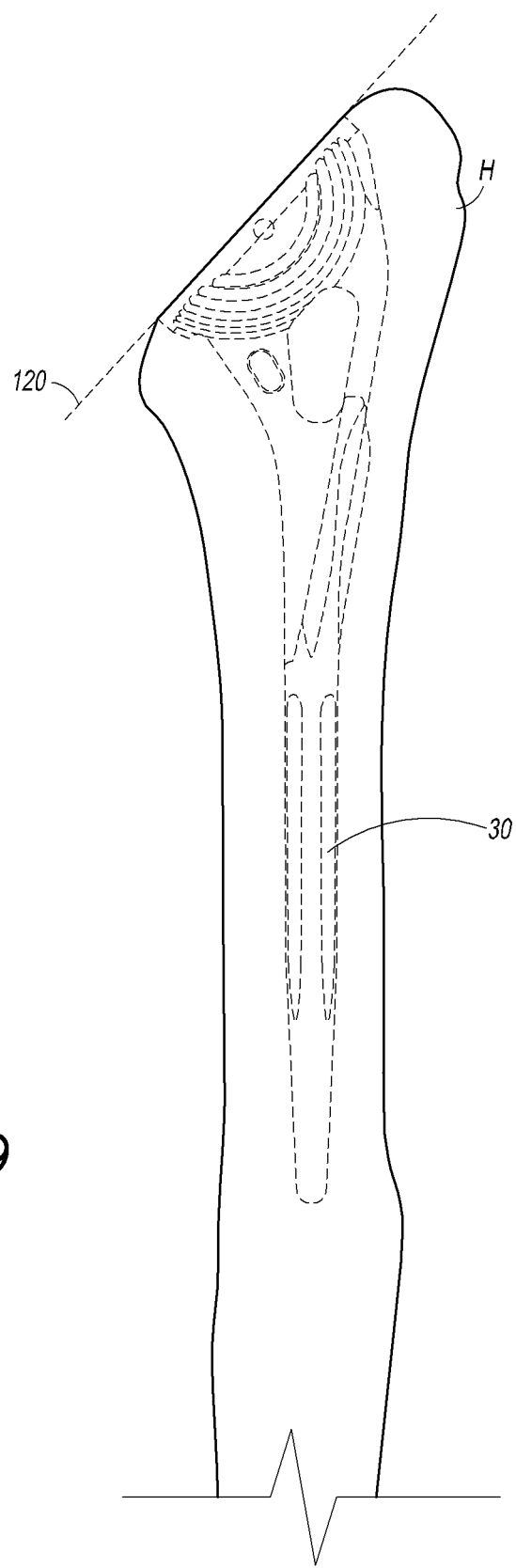
FIGS. 19-22 illustrate the use of the reverse and anatomic shoulder prostheses of FIGS. 1A and 2A, for example, in an anatomic-to-reverse conversion procedure.
Figure 20:
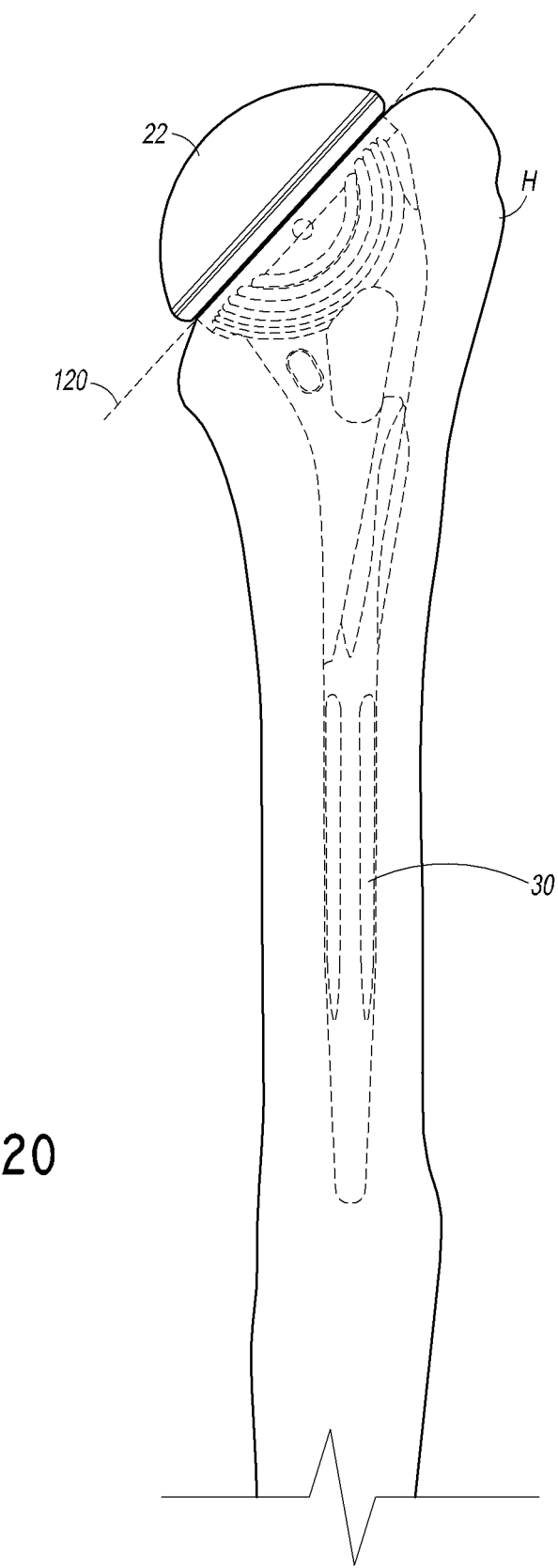
Figure 21:
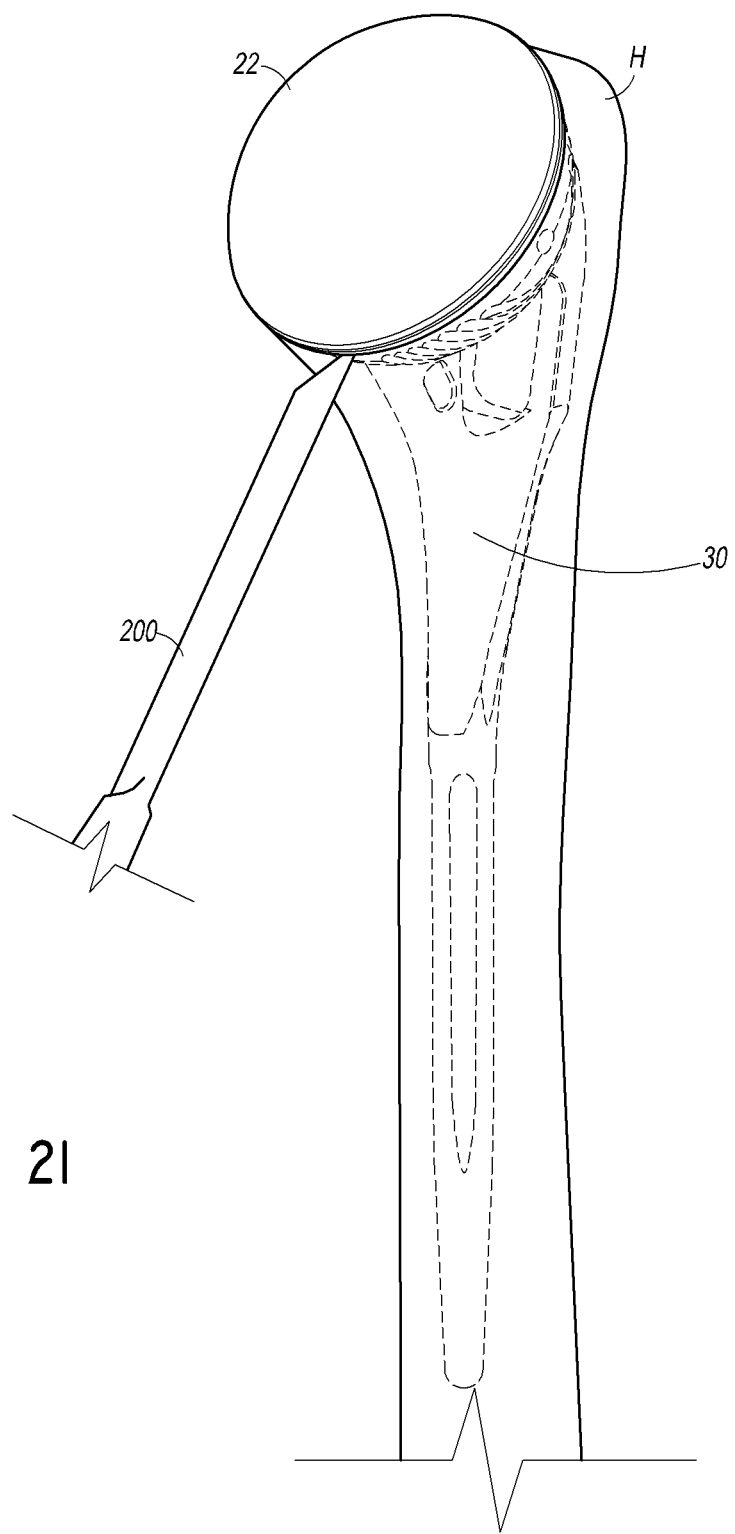
Figure 22:
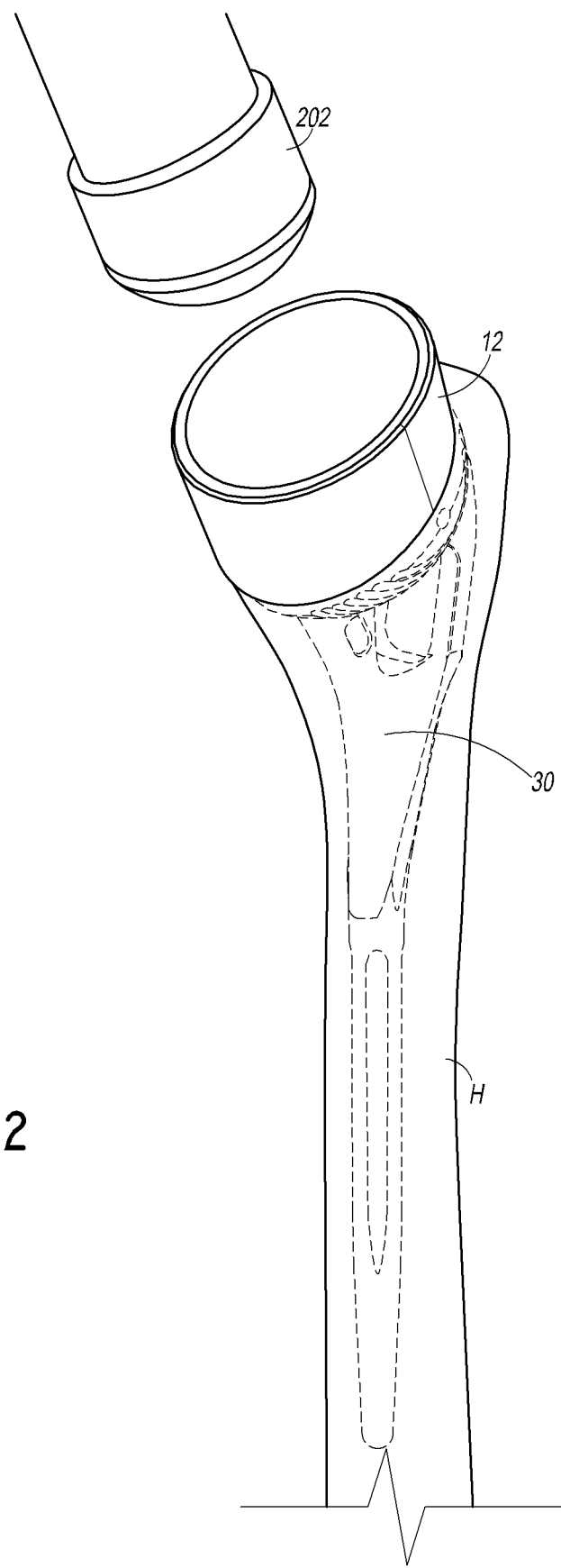

FIG. 18 illustrates a schematic of a natural human humerus H, and FIG. 19 illustrates the stem 30 implanted in the humerus H. As shown in FIG. 19, the natural humeral head has been resected. Resection plane 120 is the surface from which bone has been removed and the external surface of the remaining bone. With a standard shoulder prosthesis, when a surgeon desires to convert a primary anatomic shoulder prosthesis into a reverse shoulder prosthesis, he or she must typically remove the entire prosthesis, thereby risking further weakening the bone. However, using a modular system such as implants 10 and 20, the surgeon may leave the stem 30 implanted in the bone and simply replace the anatomic insert 22 with the reverse insert 12. FIGS. 20-22 illustrate an example procedure for converting a modular anatomic shoulder implant 20 into a modular reverse shoulder implant 10. As illustrated in FIG. 21, the anatomic insert 22 may be removed using a wedge or similar instrument 200. The reverse insert 12 can be inserted into direct engagement with the stem face 36, for example, impacted into place using an impactor 202 as shown in FIG. 22.

As shown in FIG. 19, the resection plane 120 can be flush or substantially flush with the stem face 36, i.e., with the peripheral rim 38 of the stem face 36, when the stem 30 is implanted in the humerus H. The interface between the stem 30 and the anatomic insert 22 in the anatomic prosthesis and the interface between the stem 30 and the reverse insert 12 in the reverse prosthesis are substantially flush with the resection plane 120. The modularity of the system can therefore be located at the resection plane and the conversion from an anatomic prosthesis to a reverse prosthesis can occur at the resection plane. In embodiments, instrumentation can be used to measure the angle of the resection plane so that the proper stem may be selected. The modularity of the system could alternatively be located slightly above the resection plane 120. The surgeon may then remove the anatomic insert 22 and implant the reverse insert 12 without having to remove a component that may have integrated into the patient's bony anatomy and without having to perform additional reaming or other bone preparation. This can advantageously help reduce or inhibit excessive patient bone loss.

In an example method for shoulder surgery, a unitary stem is provided. The unitary stem includes a distal portion and a proximal portion. The proximal portion includes a stem face that is configured to directly couple to a reverse shoulder insert and an anatomical shoulder insert. A surgeon or other user chooses intra-operatively to implant the reverse shoulder insert or the anatomical shoulder insert. The surgeon or other user implants a two-component shoulder system that is selected from the group consisting of a stem directly attached to the reverse shoulder insert and a stem directly attached to the anatomical shoulder insert.

In another example method for shoulder surgery, a stem of a humeral component shoulder system is implanted at least partially in a medullary canal of a humerus. The stem is adapted to directly interface with a one-component reverse shoulder insert and an anatomical shoulder insert. A surgeon or other user chooses intra-operatively to implant a one-component reverse shoulder insert or an anatomical shoulder insert. The surgeon or other user directly couples the chosen insert to the stem.

In another example method for shoulder surgery, a unitary stem is disposed at least partially in a medullary canal of a humerus. A surgeon or other user selects a reverse shoulder insert or an anatomical shoulder insert. The reverse shoulder insert includes a body with a concave articular surface on one side and an engagement structure projecting from a side of the body opposite the concave surface. The surgeon or other user implants the insert that has been chosen by directly coupling the chosen insert to the stem.

In an example method for revision shoulder surgery, an anatomical shoulder insert is removed from a unitary stem implanted in a patient's humerus to expose a proximal face of the stem. A reverse shoulder insert is directly coupled to the proximal face.

Implants of the present disclosure may be designed and/or manufactured with computer-assisted image method. Patient specific implants (PSI) include, briefly, obtaining images of patient anatomy through, for example, MRI, CT, or x-ray images. These images may then be used to create patient specific prosthesis components including stems, humeral heads, reverse inserts, and stemless shoulder components/implants. Further, patient specific guides, instruments such as graft cutter, and templates can also be provided by various CAD programs and/or commercially available software. The PSI are generally formed using computer modeling for matching a three-dimensional image of the patient's anatomy by the methods discussed above.

Alternatively PSI imaging may be used to provide a virtual model of the patient's anatomy, enabling surgeons to see in three-dimensions how a specific implant will fit into the patient's anatomy. The implant and/or the associated graft can then be altered or tailored to the surgeon's preference prior to sending along the imaging data to manufacture the implant, graft, guides, instruments, or template.

With the modular system of the present disclosure, the surgeon can advantageously decide intra-operatively whether to implant the anatomic insert 22 or reverse insert 12. In some cases, a surgeon may believe that a patient is a candidate for an anatomic prosthesis based on, for example, pre-operative examination and imaging, and may prepare for such a procedure. However, during the procedure, the surgeon may determine that a reverse prosthesis is necessary or desired instead. With some previously available prostheses, in such a situation the surgeon may need to obtain an entirely different prosthesis, which may not be possible once the surgery has begun. Even if the surgeon pre-operatively selected a modular system, the surgeon may need to prepare the bone differently for the reverse prosthesis component(s) and may not have the appropriate tools, resources, or time to do so if an anatomic prosthesis procedure was planned. With the systems of the present disclosure, the surgeon can select which insert to use, or can change from a planned anatomic prosthesis to a reverse prosthesis, during the procedure. Further, the kit of the present disclosure may be used when converting from an anatomical shoulder system to a reverse shoulder system.

In some embodiments, a kit includes the stem 30, the anatomic insert 22, and the reverse insert 12. Providing both inserts 12, 22 in a kit can advantageously allow the surgeon to select whether to use the anatomic insert 22 or reverse insert 12 pre-operatively or intra-operatively.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations are to be interpreted broadly based on the language employed and not limited to the examples described in the present specification or during the prosecution of the application, which examples are to be construed as non-exclusive.

We claim:

1. A humeral anchor for a shoulder prosthesis comprising:
    a distal portion configured to be anchored in a humerus;
    a proximal portion having a shape that is generally half-sphere and including a proximal face, wherein the proximal face comprises:
        a first engagement feature including a cavity configured to couple a reverse shoulder insert having a concave proximal portion to the humeral anchor, and
        a second engagement feature including a recess sized and configured to receive a protrusion for coupling an anatomical shoulder insert having a convex proximal portion to the humeral anchor; and
    a metaphyseal portion disposed between the distal portion and the proximal portion, the metaphyseal portion including:
        a plurality of lateral arms, and
        a medial arm positioned medically relative to a distal end of the distal portion,
    wherein a notch is defined between proximal end of the medial arm and the proximal portion, the notch sized and configured to engage a suture, and
    wherein a window sized and configured to receive a bone graft is defined between a lateral edge of the medial arm, a medial edge of each lateral arm of the plurality of lateral arms, and the proximal portion.

2. A kit comprising the humeral anchor of claim 1, and further comprising:
    a reverse insert having a proximal portion and a distal portion, the proximal portion of the reverse insert including a concave surface configured to engage a glenosphere and the distal portion of the reverse insert configured to engage the engagement feature of the proximal face of the humeral anchor.

3. The kit of claim 2, wherein the cavity defined by the proximal face of the humeral anchor has an inner dimension, the distal portion of the reverse insert has an outer dimension, whereby an interference fit is provided between the distal portion of the reverse insert and the cavity defined by the proximal face of the humeral anchor when the reverse insert is engaged with the engagement feature of the humeral anchor.

4. A kit comprising the humeral anchor of claim 1, and further comprising:
an anatomical insert having a proximal portion including a convex surface and a distal portion configured to couple to the proximal face of the humeral anchor.

5. The humeral anchor of claim 1, wherein the distal portion of the humeral anchor comprises a stem sized and configured to be received in a medullary canal of a humerus.

6. The humeral anchor of claim 5, wherein the plurality of lateral arms includes a first lateral arm and a second lateral arm spaced apart from the first lateral arm.

7. The humeral anchor of claim 6, wherein a gap is defined between the first lateral arm and the second lateral arm, the gap in communication with the window.

8. A kit for a shoulder prosthesis comprising:
a stem comprising a unitary body having a shaft portion configured to be anchored in a medullary canal of a humerus and a proximal portion, the proximal portion including a stem face, wherein the stem face comprises an engagement feature configured to directly couple to a reverse shoulder insert having a concave proximal portion, and wherein the stem face is further configured to directly couple with an anatomical shoulder insert having a convex proximal portion; and
a bone graft cutter comprising:
a drill guide, and
a cutting cap.

9. The kit of claim 8, wherein the drill guide includes at least four holes provided at different angles.

10. The kit of claim 8, wherein the cutting cap is shaped to be received therein the drill guide.

11. The kit of claim 8, further comprising a drill.

12. The kit of claim 8, further comprising a mallet.

13. The kit of claim 8, further comprising a bone graft.

14. The kit of claim 13, wherein the bone graft is shaped to be received in the stem.

15. The kit of claim 13, wherein the bone graft is selected from the group consisting of bone, stem cells, ceramic, polymer and porous metal.

16. The kit of claim 13, wherein the bone is selected from the group consisting of an allograft and autograft.

17. A kit for a shoulder prosthesis comprising:
the humeral anchor according to claim 1; and
a reverse shoulder insert having a concave proximal portion,
wherein the first engagement feature of the proximal face is configured to couple to the reverse shoulder insert.

18. The kit of claim 17, wherein the distal portion of the humeral anchor includes a stem.

19. The kit of claim 17, further comprising an anchor holder configured to hold the humeral anchor during placement in the humerus.

20. The kit of claim 19, wherein the anchor holder comprises at least one compression feature configured for retaining the first engagement feature of the proximal face.

21. The kit of claim 20, wherein the anchor holder is in a snap fit arrangement with the first engagement feature of the proximal face.

22. The kit of claim 20, wherein the anchor holder is in an interference fit arrangement with the first engagement feature of the proximal face.

* * * * *